US011632948B2

(12) United States Patent
Gibson et al.

(10) Patent No.: US 11,632,948 B2
(45) Date of Patent: Apr. 25, 2023

(54) RECRYSTALLIZATION INHIBITOR

(71) Applicant: THE UNIVERSITY OF WARWICK, Coventry (GB)

(72) Inventors: Matthew I. Gibson, Coventry (GB); Ben Graham, Coventry (GB); Trisha L. Bailey, Coventry (GB)

(73) Assignee: THE UNIVERSITY OF WARWICK, Coventry (GB)

( * ) Notice: Subject to any disclaimer, the term of this patent is extended or adjusted under 35 U.S.C. 154(b) by 598 days.

(21) Appl. No.: 16/619,676

(22) PCT Filed: Jun. 5, 2018

(86) PCT No.: PCT/GB2018/051530
§ 371 (c)(1),
(2) Date: Dec. 5, 2019

(87) PCT Pub. No.: WO2018/224816
PCT Pub. Date: Dec. 13, 2018

(65) Prior Publication Data
US 2020/0178517 A1    Jun. 11, 2020

(30) Foreign Application Priority Data
Jun. 6, 2017    (GB) ..................... 1708999

(51) Int. Cl.
| A01N 1/02 | (2006.01) |
| A23B 4/08 | (2006.01) |
| A23B 7/05 | (2006.01) |
| A23G 9/38 | (2006.01) |
| A23L 3/37 | (2006.01) |
| C07K 7/06 | (2006.01) |
| C07K 7/08 | (2006.01) |

(52) U.S. Cl.
CPC .............. *A01N 1/0221* (2013.01); *A23B 4/08* (2013.01); *A23B 7/05* (2013.01); *A23G 9/38* (2013.01); *A23L 3/37* (2013.01); *C07K 7/06* (2013.01); *C07K 7/08* (2013.01); *A23V 2002/00* (2013.01)

(58) Field of Classification Search
CPC .......... A01N 1/0221; A23B 4/08; A23B 7/05; A23G 9/38; A23L 3/37; A23V 2002/00; C07K 7/06; C07K 7/08
See application file for complete search history.

(56) References Cited

U.S. PATENT DOCUMENTS

| 5,071,741 A | 12/1991 | Brockbank |
| 5,358,931 A | 10/1994 | Rubinsky et al. |
| 5,620,732 A * | 4/1997 | Clemmings ............... A23L 3/37 |
| | | 426/660 |
| 5,897,987 A | 4/1999 | Oliver et al. |
| 6,593,138 B1 | 7/2003 | Oliver et al. |
| 7,112,576 B1 | 9/2006 | Hubel |
| 9,458,424 B2 | 10/2016 | Comhaire et al. |
| 2007/0259327 A1 | 11/2007 | Iwanaga et al. |
| 2010/0151096 A1 | 6/2010 | Damodaran |
| 2013/0267008 A1 | 10/2013 | Shon et al. |
| 2015/0017628 A1 | 1/2015 | Gibson et al. |
| 2015/0373968 A1 | 12/2015 | Ben et al. |

FOREIGN PATENT DOCUMENTS

| WO | 2014/175838 | 10/2014 |
| WO | 2017/066454 | 4/2017 |

OTHER PUBLICATIONS

Bradley et al. Lung Collagen Composition and Synthesis (1973) The Journal of Biological Chemistry vol. 219, No. 9, Issue of May 10, pp. 2674-2683, 1974.
Drake et al. "Reassessment of the electronic circular dichroism criteria for random coil conformations of poly(L-lysine) and the implications for protein folding and denaturation studies" Biophysical Chemistry, 31 (1988) 143-146.
Adzhubei, Alexei A., Michael JE Sternberg, and Alexander A. Makarov. "Polyproline-II helix in proteins: structure and function." Journal of molecular biology 425.12 (2013): 2100-2132.
Ashraf, M. F. M. R., and Majid R. Foolad. "Roles of glycine betaine and proline in improving plant abiotic stress resistance." Environmental and experimental botany 59.2 (2007): 206-216.
Brockbank, K. & Taylor, M. "Cryopreservation: An emerging paradigm change". Chapter 8 Tissue Preservation in Adv. Biopreservation 5, 157-196 (2007).
Budke, Carsten, and Thomas Koop. "Ice recrystallization inhibition and molecular recognition of ice faces by poly (vinyl alcohol)." ChemPhysChem 7.12 (2006): 2601-2606.
Capicciotti, Chantelle J., et al. "Potent inhibition of ice recrystallization by low molecular weight carbohydrate-based surfactants and hydrogelators." Chemical Science 3.5 (2012): 1408-1416.
Chao, Heman, Peter L. Davies, and John F. Carpenter. "Effects of antifreeze proteins on red blood cell survival during cryopreservation." Journal of experimental biology 199.9 (1996): 2071-2076.
Congdon, Thomas, Rebecca Notman, and Matthew I. Gibson. "Antifreeze (glyco) protein mimetic behavior of poly (vinyl alcohol): detailed structure ice recrystallization inhibition activity study." Biomacromolecules 14.5 (2013): 1578-1586.

(Continued)

*Primary Examiner* — Marcela M Cordero Garcia
(74) *Attorney, Agent, or Firm* — Meunier Carlin & Curfman LLC

(57) ABSTRACT

The present invention relates to methods for preventing or inhibiting ice recrystallisation in substances (e.g. biological materials and food products) which are susceptible to ice crystal growth upon cryopreservation and/or thawing therefrom. The methods relate to the use of compositions comprising poly(proline) or a variant or derivative thereof. Also provided are kits and compositions comprising poly(proline) which can be used in the methods of the invention.

17 Claims, 9 Drawing Sheets
Specification includes a Sequence Listing.

(56) References Cited

OTHER PUBLICATIONS

Czechura, Pawel, et al. "The importance of hydration for inhibiting ice recrystallization with C-linked antifreeze glycoproteins." Journal of the American Chemical Society 130.10 (2008): 2928-2929.
Deller, Robert C., et al. "Enhanced non-vitreous cryopreservation of immortalized and primary cells by ice-growth inhibiting polymers." Biomaterials science 4.7 (2016): 1079-1084.
Deller, Robert C., et al. "Synthetic polymers enable non-vitreous cellular cryopreservation by reducing ice crystal growth during thawing." Nature communications 5.1 (2014): 3244.
Fowler, Alex, and Mehmet Toner. "Cryo-injury and biopreservation." Annals of the New York Academy of Sciences 1066.1 (2006): 119-135.
Geng, Hongya, et al. "Graphene Oxide Restricts Growth and Recrystallization of Ice Crystals." Chem. Int. Ed. 56, (2017): 997-1001.
Gibson, Matthew I. "Slowing the growth of ice with synthetic macromolecules: beyond antifreeze (glyco) proteins." Polymer Chemistry 1.8 (2010): 1141-1152.
Gibson, Matthew I., and Neil R. Cameron. "Experimentally facile controlled polymerization of N-carboxyanhydrides (NCAs), including O-benzyl-L-threonine NCA." Journal of Polymer Science Part A: Polymer Chemistry 47.11 (2009): 2882-2891.
Gibson, Matthew I., et al. "Inhibition of ice crystal growth by synthetic glycopolymers: implications for the rational design of antifreeze glycoprotein mimics." Biomacromolecules 10.2 (2009): 328-333.
Gutierrez, Erik, et al. "eIF5A promotes translation of polyproline motifs." Molecular cell 51.1 (2013): 35-45.
Heng, Boon Chin, et al. "Loss of viability during freeze-thaw of intact and adherent human embryonic stem cells with conventional slow-cooling protocols is predominantly due to ␣ apoptosis rather than cellular necrosis." Journal of biomedical science 13.3 (2006): 433-445.
Iwatani, Misa, et al. "Dimethyl sulfoxide has an impact on epigenetic profile in mouse embryoid body." Stem cells 24.11 (2006): 2549-2556.
Kawai, Kazuaki, et al. "DNA methylation by dimethyl sulfoxide and methionine sulfoxide triggered by hydroxyl radical and implications for epigenetic modifications." Bioorganic & medicinal chemistry letters 20.1 (2010): 260-265.
Knight, Charles A., John Hallett, and A. L. DeVries. "Solute effects on ice recrystallization: an assessment technique." Cryobiology 25.1 (1988): 55-60.
Kwan, Ann H-Y., et al. "Solution structure of a recombinant type I sculpin antifreeze protein." Biochemistry 44.6 (2005): 1980-1988.
Liu, Suhuai, et al. "In vitro studies of antifreeze glycoprotein (AFGP) and a C-Tinked AFGP analogue." Biomacromolecules 8.5 (2007): 1456-1462.
Lopes, Jose LS, et al. "Distinct circular dichroism spectroscopic signatures of polyproline II and unordered secondary structures: applications in secondary structure analyses." Protein Science 23.12 (2014): 1765-1772.
Marcellini, Moreno, et al. "Time-Lapse, in situ imaging of ice crystal growth using confocal microscopy." ACS omega 1.5 (2016): 1019-1026.
Matsumura, Kazuaki, and Suong-Hyu Hyon. "Polyampholytes as low toxic efficient cryoprotective agents with antifreeze protein properties." Biomaterials 30.27 (2009): 4842-4849.
Matsumura, Kazuaki, et al. "Cryopreservation of a two-dimensional monolayer using a slow vitrification method with polyampholyte to inhibit ice crystal formation." ACS Biomaterials Science & Engineering 2.6 (2016): 1023-1029.
Mazur, Peter, et al. "Survival of hamster tissue culture cells after freezing and thawing: Interactions between protective solutes and cooling and warming rates." Cryobiology 6.1 (1969): 1-9.
Mazur, Peter. "Cryobiology: the freezing of biological systems." Science 168.3934 (1970): 939-949.

Merrifield, Robert B. "Solid phase peptide synthesis. I. The synthesis of a tetrapeptide." Journal of the American Chemical Society 85.14 (1963): 2149-2154.
Mikhonin, Aleksandr V., et al. "UV resonance Raman determination of polyproline II, extended 2.51-helix, and β-sheet ψ angle energy landscape in poly-L-lysine and poly-L-glutamic acid." Journal of the American Chemical Society 127.21 (2005): 7712-7720.
Mitchell, Daniel E., and Matthew I. Gibson. "Latent ice recrystallization inhibition activity in nonantifreeze proteins: Ca2+-activated plant lectins and cation-activated antimicrobial peptides." Biomacromolecules 16.10 (2015): 3411-3416.
Mitchell, Daniel E., et al. "Quantitative study on the antifreeze protein mimetic ice growth inhibition properties of poly (ampholytes) derived from vinyl-based polymers." Biomaterials Science 2.12 (2014): 1787-1795.
Mitchell, Daniel E., Neil R. Cameron, and Matthew I. Gibson. "Rational, yet simple, design and synthesis of an antifreeze-protein inspired polymer for cellular cryopreservation." Chemical Communications 51.65 (2015): 12977-12980.
Protein Circular Dichroism Data Bank. CD0004553000 (2016). Available on-line at: https://pcddb.cryst.bbk.ac.uk/deposit/CD0004553000.
Seth, Gargi. "Freezing mammalian cells for production of biopharmaceuticals." Methods 56.3 (2012): 424-431.
Shu, Zhiquan, Shelly Heimfeld, and Dayong Gao. "Hematopoietic SCT with cryopreserved grafts: adverse reactions after transplantation and cryoprotectant removal before infusion." Bone marrow transplantation 49.4 (2014): 469-476.
Stéphenne, Xavier, Mustapha Najimi, and Etienne M. Sokal. "Hepatocyte cryopreservation: is it time to change the strategy?" World journal of gastroenterology: WJG 16.1 (2010): 1-14.
Stokich, Blake, et al. "Cryopreservation of hepatocyte (HepG2) cell monolayers: Impact of trehalose." Cryobiology 69.2 (2014): 281-290.
Tam, Roger Y., et al. "Hydration Index—a Better Parameter for Explaining Small Molecule Hydration in Inhibition of Ice Recrystallization." Journal of the American Chemical Society 130.51 (2008): 17494-17501.
Walsh, Gary. "Biopharmaceutical benchmarks 2006." Nature biotechnology 24.7 (2006): 769-776.
Wilhelm, Patrick, et al. "A crystal structure of an oligoproline PPII-helix, at last." Journal of the American Chemical Society 136.45 (2014): 15829-15832.
Wowk, Brian, et al. "Vitrification enhancement by synthetic ice blocking agents." Cryobiology 40.3 (2000): 228-236.
Xu, Qin, et al. "Apolipoprotein E4 domain interaction occurs in living neuronal cells as determined by fluorescence resonance energy transfer." Journal of Biological Chemistry 279.24 (2004): 25511-25516.
Xu, Xia, et al. "The roles of apoptotic pathways in the low recovery rate after cryopreservation of dissociated human embryonic stem cells." Biotechnology progress 26.3 (2010): 827-837.
Yoshiba, Yoshu, et al. "Regulation of levels of proline as an osmolyte in plants under water stress." Plant and Cell Physiology 38.10 (1997): 1095-1102.
Corcilius, Leo, et al. "Synthesis of peptides and glycopeptides with polyproline II helical topology as potential antifreeze molecules." Bioorganic & Medicinal Chemistry 21.12 (2013): 3569-3581.
DeVries, Arthur L., Stanley K. Komatsu, and Robert E. Feeney. "Chemical and physical properties of freezing point-depressing glycoproteins from Antarctic fishes." Journal of Biological Chemistry 245.11 (1970): 2901-2908.
Knight, C. A., E. Driggers, and A. L. DeVries. "Adsorption to ice of fish antifreeze glycopeptides 7 and 8." Biophysical Journal 64.1 (1993): 252-259.
Knight, Charles A., Dingyi Wen, and Richard A. Laursen. "Nonequilibrium antifreeze peptides and the recrystallization of ice." Cryobiology 32.1 (1995): 23-34.
Lin, Feng-Hsu, et al. "Structural modeling of snow flea antifreeze protein." Biophysical Journal 92.5 (2007): 1717-1723.

(56) References Cited

OTHER PUBLICATIONS

Lin, Yuan, John G. Duman, and Arthur L. DeVries. "Studies on the structure and activity of low molecular weight glycoproteins from an Antarctic fish." Biochemical and Biophysical Research Communications 46.1 (1972): 87-92.
Mok, Yee-Foong, et al. "Structural basis for the superior activity of the large isoform of snow flea antifreeze protein." Biochemistry 49.11 (2010): 2593-2603.
Nguyen, Dat H., et al. "The dynamics, structure, and conformational free energy of proline-containing antifreeze glycoprotein." Biophysical Journal 82.6 (2002): 2892-2905.
International Search Report and Written Opinion issued for Application No. PCT/GB2018/051530, dated Jul. 27, 2018.
Search Report issued for Application No. GB 1708999.6, dated Dec. 6, 2017.
Official Action in connection to European Application No. 18732414.0, dated Jan. 25, 2021.

\* cited by examiner

Figures 3F - 3G
Fig. 3F
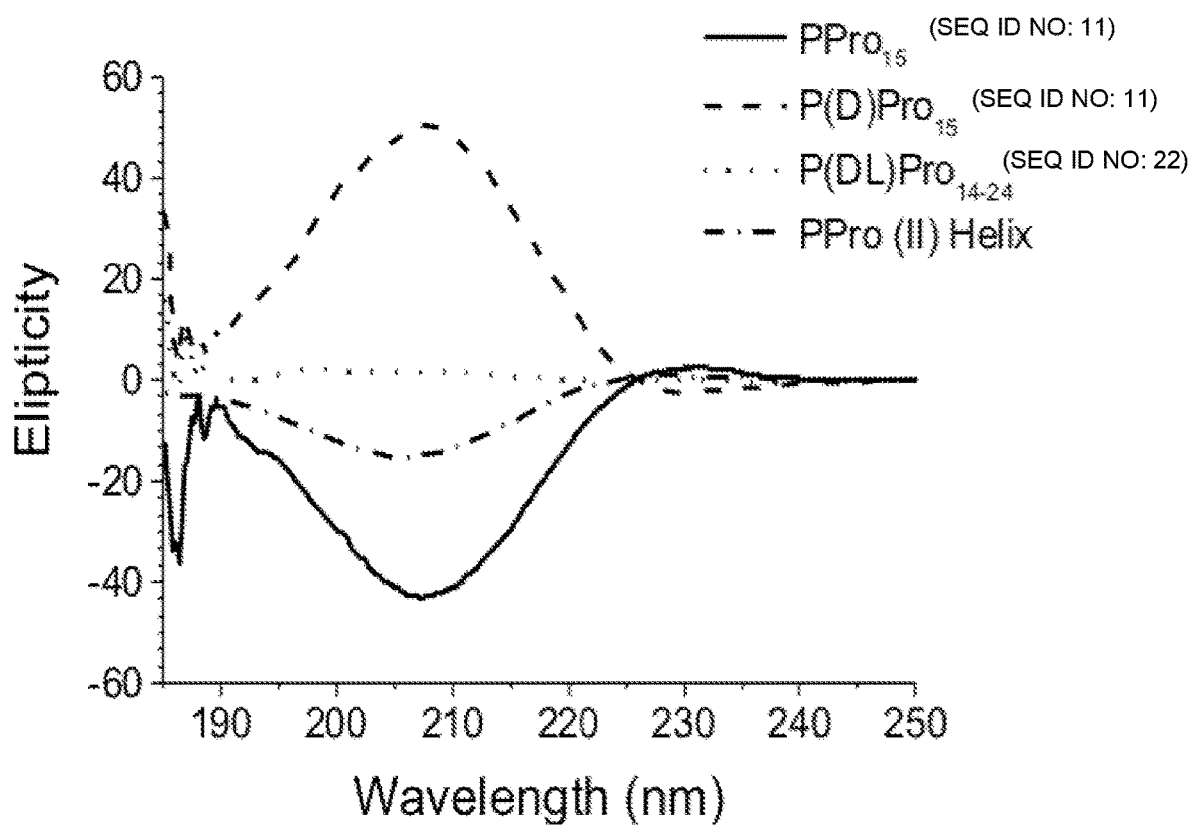
Fig. 3G
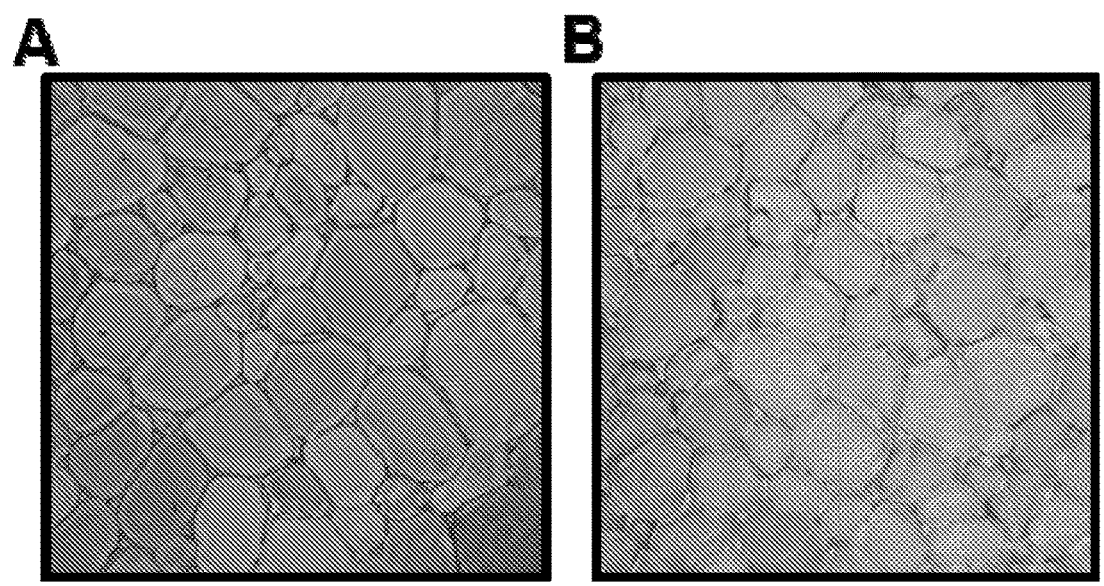

RECRYSTALLIZATION INHIBITOR

CROSS-REFERENCE TO RELATED APPLICATIONS

This application is a national stage application filed under 35 U.S.C. § 371 of PCT/GB2018/051530, filed Jun. 5, 2018, which claims the benefit of priority to Great Britain Patent Application No. 1708999.6, filed Jun. 6, 2017, the contents of each are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 133092-02_US_ST25.txt, date recorded: Aug. 10, 2022, file size ~12.3 kilobytes).

The present invention relates to methods for preventing or inhibiting ice recrystallisation in substances (e.g. biological materials and food products) which are susceptible to ice crystal growth upon cryopreservation and/or thawing therefrom. The methods relate to the use of compositions comprising poly(proline) or a variant or derivative thereof. Also provided are kits and compositions comprising poly(proline) which can be used in the methods of the invention.

Tissue engineering, gene therapy, therapeutic protein production and transplantation all rely on our ability to successfully store and transport cellular material [1]. For example, in the production of recombinant therapeutic proteins, a specific cell line for each protein must be developed [2]. Given that any in vitro culture of cells will undergo phenotypic and genetic changes when propagated for long periods of time, it is neither possible nor practical to maintain a constantly-growing culture of cells [3]. The only practical solution to this is to cryopreserve cells, i.e. freezing them such that all metabolic processes stop. In particular, the ability to cryopreserve cells in monolayer format would facilitate drug development by providing phenotypically-identical cells for assays.

In order to avoid unwanted ice damage, significant volumes of cryoprotectants such as DMSO must usually be added to cells. For example, formulations containing 5-10% DMSO are the standard protocol which is utilized in freezing cells in solution and in reducing cryo-injury by moderating the increase in solute concentration during freezing [11-13]. However, such concentrations are generally intrinsically toxic [4-5]. Furthermore, the repeated use of DMSO has been shown to have an impact on the epigenetic profile of cells, specifically the alteration of DNA methylation profiles, which results in phenotypic changes [6-7].

Additionally, the survival rates which are obtainable using DMSO with adherent human cells, such as embryonic stem cells, are currently too low to be of practical use [8-10].

Whilst DMSO clearly has some valuable uses in the context of cell preservation, for it to be capable of being used more widely, improvements in cell yield will have to be made in order to outweigh the issues associated with its toxicity.

A key contributor to cell death during cryopreservation is ice recrystallization (growth); this is not affected by traditional cryoprotectants and additives.

Antifreeze (glyco)proteins (AF(G)Ps) from extremophile species are potent ice recrystallization inhibitors (IRI), but are unsuitable for cryopreservation applications due to their potential toxicity/immunogenicity. Their secondary effect of dynamic ice shaping (DIS) leads to 'needle like' ice crystals which pierce cell membranes and reduce cell viability [14]. DeVries et al. [30] notes that such proteins are composed primarily of threonine, alanine, N-acetylgalactosamine and galactose; and that the results disclosed therein indicate that galactose residues, specifically their hydroxyl groups, are necessary for function.

A number of further AF(G)P sequences are disclosed in Knight et al. [42] (see Table 1). Knight notes that all of these peptides had a 100% alpha-helical structure, with the exception of peptide S12 which had an Ala→Pro substitution and which eliminated the antifreeze activity of the peptide. Knight also tested a number of synthetic polymers, including poly-L-histidine, poly-L-aspartic acid, poly-L-asparagine, poly-L-hydroxyproline, polyvinylalcohol (PVA), polyacrylic acid and polyvinylpyrrolidone; the best was PVA.

Synthetic polymers which have no structural similarities to AF(G)Ps but possess potent IRI properties have recently emerged as a new paradigm for controlling ice growth [15]. The most active one studied to date is poly(vinyl alcohol) (PVA), which can inhibit ice growth at less than 0.1 mg·mL$^{-1}$ and has been shown by Gibson et al. to enhance the cryopreservation of non-adherent cells [16-18]. It is hypothesized that PVA may function by recognition between the regularly-spaced hydroxyl groups and the growing ice crystal [19].

Other polymer materials have also been studied. Matsumura et al. have developed polyampholytes (mixed positive/negative charges) [20-21] which are cryoprotectants despite having only moderate IRI activity [22-23]. Wang et al. have demonstrated the significant IRI activity of graphene oxide in inhibiting the growth and recrystallisation of ice crystals in cell culture media at low concentrations [24]. Ben et al. have developed low molecular weight surfactants which also inhibit ice growth [25].

Whilst AF(G)Ps clearly engage specific ice crystal faces, it is clear that IRI can be engineered without affecting ice morphology, potentially by inhibiting the transfer of water between the bulk/quasi liquid layer at the ice surface [26]. Crucial to IRI is the correct display of hydrophobic groups whilst avoiding micellization/precipitation. Mitchell et al. have shown that Nisin A, a short antimicrobial peptide has pH dependent IRI activity which seems to be due to the formation of an amphipathic structure [27].

Currently, there are no crystal structures for AF(G)Ps.

In summary, therefore, a wide variety of synthetic IRIs have been previously been produced having a number of diverging structures.

The inventors have now discovered that poly(proline) has significant IRI activity and hence that it can be used for cryopreservation and in cryopreservative compositions. In contrast to the disclosures of DeVries [30] (which taught that hydroxyl groups were necessary for IRI activity), poly(proline) has now been found by the inventors to be more active than poly(hydroxyproline), with smaller MLGS (mean largest grain size) and functioning at lower concentrations. This is a significant observation as it confirms that hydroxyl groups are not essential for activity or for 'recognition' of the ice surface in IRI active compounds, and that the design of new IRI macromolecules should not be limited to poly-ols. Furthermore, there are no obvious hydrogen bond donor sites on poly(proline), which has no amide NH's.

It is therefore an object of the invention to provide methods and compositions which overcome one or more of the above-mentioned deficiencies.

In particular, it is an object of the invention to provide methods and compositions which prevent or inhibit ice recrystallisation in substances, e.g. biological materials and frozen food products, thereby facilitating increased cell viability in biological materials following cryopreservation and improved texture and/or flavour in frozen food products.

In one embodiment, the invention provides a method of preventing or inhibiting ice recrystallisation in a substance which is susceptible to ice crystal growth upon cryopreservation and/or warming or thawing therefrom, the method comprising the step:
(i) treating the substance with a composition comprising poly(proline) or a variant or derivative thereof.

The invention also provides a method of treating a substance which is susceptible to ice crystal growth upon cryopreservation and/or warming or thawing therefrom, the method comprising the step:
(i) treating the substance with a composition comprising poly(proline) or a variant or derivative thereof.

In another embodiment, the invention provides a method of cryopreserving a substance which is susceptible to ice crystal growth upon cryopreservation and/or warming or thawing therefrom, the method comprising the steps:
(i) treating the substance with a composition comprising poly(proline) or a variant or derivative thereof;
(ii) reducing the temperature of the treated substance to a cryopreserving temperature; and optionally
(iii) storing the treated substance at the cryopreserving temperature.

In another embodiment, the invention provides a method of warming or thawing a cryopreserved substance, the method comprising the step:
(i) warming or thawing a cryopreserved substance, wherein the cryopreserved substance is one which has been treated with poly(proline) or a variant or derivative thereof.

In another embodiment, the invention provides a method of reducing cell damage during the warming or thawing of a cryopreserved substance comprising biological material, the method comprising the step:
(i) warming or thawing the cryopreserved substance comprising biological material,
wherein the cryopreserved substance is one which has been treated with poly(proline) or a variant or derivative thereof.

The invention also provides the use of poly(proline), or a variant or derivative thereof, as an ice recrystallisation inhibitor.

In a further embodiment, the invention provides a composition comprising poly(proline), or a variant or derivative thereof, for preventing or reducing the recrystallization of ice crystals.

As used herein, the term "poly(proline)" refers to a homogeneous or heterogeneous mixture of polymers which consist substantially or exclusively of linear chains of proline residues, the polymers having the general structure:

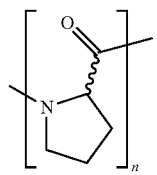

Formula I wherein n=3-200 (SEQ ID NO: 1). The molecular mass of proline is 115.13. Preferably, n is 3-150 (SEQ ID NO: 2) or 5-100 (SEQ ID NO: 3); more preferably 10-100 (SEQ ID NO: 4), 10-50 (SEQ ID NO: 5) or 10-25 (SEQ ID NO: 6); and even more preferably 10-20 (SEQ ID NO: 7) or 11-15 (SEQ ID NO: 8).

In some embodiments, n is 10 (SEQ ID NO: 9), 11 (SEQ ID NO: 10), 15 (SEQ ID NO: 11), 19 (SEQ ID NO: 12), 20 (SEQ ID NO: 13) or 21 (SEQ ID NO: 14). Most preferably, n=11 (SEQ ID NO: 10).

The term "poly(proline)" includes stereoisomers of proline. In particular, the proline monomers in the poly(proline) polymers may solely be the L-proline isomer or D-proline isomer, or a mixture of the L- and D-isomers. Preferably, the proline monomers in the polyproline polymer are solely L-proline isomers or solely D-proline isomers.

Preferably, the poly(proline) polymer is a homopolymer. In other embodiments, the poly(proline) polymer is a heteropolymer. Preferably, the poly(proline) polymer consists of proline residues only.

Poly(proline) is available from Sigma Aldrich (UK) 1,000-10,000 mwt, 10,000-30,000 mwt and >30,000 mwt (based on viscosities). These preferred molecular weight ranges equate to average n values of 9-86 (SEQ ID NO: 15), 86-261 (SEQ ID NO: 16) and >261 (SEQ ID NO: 17).

It is preferable that the poly(proline) polymer forms a poly(proline) helix, e.g. a poly(proline) I type (PPI) helix or a poly(proline) II type (PPII) helix. Most preferably, the poly(proline) polymer forms a poly(proline) II type (PPII) helix. The PPII helix is defined by ($\varphi,\psi$) backbone dihedral angles of roughly ($-75°$, $150°$) and trans isomers of the peptide bonds. For this reason, n will preferably be 3 or greater.

The term "poly(proline) polymer" encompasses polymers having the same or substantially the same length (i.e. wherein n has one value or substantially one value) and also mixtures of polymers wherein n is a range of values, such as those mentioned above.

The concentration of the poly(proline) polymer in the composition is preferably 1-50 mg/mL, more preferably 10-40, 10-30 or 10-20 mg/mL. In some embodiments (e.g. for poly(proline)$_{10}$ (SEQ ID NO: 9)), the preferred concentration is 10-20 mg/mL. In other embodiments (e.g. for poly(proline)$_{15}$ (SEQ ID NO: 11)) the preferred concentration is 5-15 mg/mL.

In some (or all) embodiments of the invention, the poly (proline) polymer may be replaced with a variant or derivative of a poly(proline) polymer. The variant or derivative of the poly(proline) polymer should be one which is substantially or fully capable of forming a poly(proline) (PP) helix, preferably a poly(proline) II type (PPII) helix. The presence or absence of a poly(proline) II type (PPII) helix may be determined by circular dichroism spectroscopy.

In some embodiments, the variant or derivative of the poly(proline) polymer may comprise one or more non-proline monomers. In these embodiments, one or more of the monomers in Formula I above may be replaced by non-proline monomers. For example, 1-20%, preferably 1-10% or 1-5% (by weight) of the poly(proline) monomers may be replaced by non-proline monomers.

Preferably, the non-proline monomers are naturally-occurring amino acids or non-naturally-occurring amino acids. These monomers will form peptide bonds with the proline monomers. Examples of such non-proline monomers include N-substituted amino acids, e.g. sarcosine.

In some embodiments, the poly(proline) polymer or variant or derivative thereof is not homo-poly(hydroxyproline). In other embodiments, the poly(proline) polymer, or variant or derivative thereof, does not comprise more than 5%, 10%, 20%, 30%, 40%, 50%, 60%, 70%, 80% or 90% (by weight) hydroxyproline monomers. In other embodiments, the poly(proline) polymer, or variant or derivative thereof, does not comprise any hydroxyproline monomers.

However, the poly(proline) polymers or variants or derivatives thereof may have been subject to other modifications, e.g. acetylation, phosphorylation and/or amidation. For example, the poly(proline) polymers, or variants or derivatives thereof, may be N-terminally acetylated.

In most embodiments, the composition is an aqueous composition or substantially an aqueous composition.

In some embodiments, the composition is a cryopreserving composition. The cryopreserving composition will, in general, be an aqueous solution, wherein water is the largest component (vol/vol). The cryopreserving composition will be one which is suitable for the preservation of biological material. Preferably, it is a physiologically-acceptable composition.

The composition may additionally comprise one or more other components. The cryopreserving composition may additionally comprise DMSO. Preferably, the amount of DMSO is 5-20% (vol/vol). In other embodiments, the cryopreserving composition comprises no DMSO or less than 1% (vol/vol) DMSO.

The cryopreserving composition may also comprise one or more other components, e.g. glycerol, trehalose, cell culture media (preferably including fetal bovine serum) and poly(ampholyte). The composition may additionally comprise one or more of the following: a buffer, e.g. PBS; an antibiotic; an anticoagulant; an antioxidant; and a pH indicator.

In a further embodiment, the invention provides a composition comprising poly(proline), or a variant or derivative thereof, for use in a method of preventing or reducing the recrystallization of ice crystals in a substance (preferably a biological substance) which is susceptible to ice crystal growth upon cryopreservation and/or warming or thawing therefrom. Preferably, the composition is one which is suitable for use in cryopreserving biological material.

Preferably the composition comprises:
(a) a mixture of one or more poly(proline) polymers, wherein n=10-20 (SEQ ID NO: 7);
(b) DMSO at a concentration of 1-10% (vol./vol.);
(c) cell culture media (preferably including fetal bovine serum); and optionally
(d) one or more additional cryoprotectants.

Also provided is a composition comprising poly(proline), or a variant or derivative thereof, for use in a method of the invention.

The "substance which is susceptible to ice crystal growth upon cryopreservation and/or thawing therefrom" is preferably biological material, a food product or a personal health care product. Such substances may comprise significant quantities of water (e.g. at least 5%, 10% or 20% water by weight) and hence ice crystals may form in such substances at cryopreserving temperatures.

As used herein, the term "biological material" relates primarily to cell-containing biological material. The term includes cells, tissues, whole organs and parts of organs.

The cells which may be used in the methods or uses of the invention may be any cells which are suitable for cryopreservation. The cells may be prokaryotic or eukaryotic cells.

The cells may be bacterial cells, fungal cells, plant cells, animal cells, preferably mammalian cells, and most preferably human cells. In some embodiments of the invention, the cells are all of the same type. For example, they are all blood cells, brain cells, muscle cells or heart cells.

In other embodiments, the biological material comprises a mixture of one or more types of cell. For example, the biological material may comprise a primary culture of cells, a heterogeneous mixture of cells or spheroids. In other embodiments, the cells are all from the same lineage, e.g. all haematopoietic precursor cells.

The cells for cryopreservation are generally live or viable cells or substantially all of the cells are live or viable. In some embodiments, the cells are isolated cells, i.e. the cells are not connected in the form of a tissue or organ.

In some preferred embodiments, the cells are adipocytes, astrocytes, blood cells, blood-derived cells, bone marrow cells, bone osteosarcoma cells, brain astrocytoma cells, breast cancer cells, cardiac myocytes, cerebellar granule cells, chondrocytes, corneal cells, dermal papilla cells, embryonal carcinoma cells, embryo kidney cells, endothelial cells, epithelial cells, erythroleukaemic lymphoblasts, fibroblasts, foetal cells, germinal matrix cells, hepatocytes, intestinal cells, keratocytes, kidney cells, liver cells, lung cells, lymphoblasts, melanocytes, mesangial cells, meningeal cells, mesenchymal stem cells, microglial cells, neural cells, neural stem cells, neuroblastoma cells, oligodendrocytes, oligodendroglioma cells, oocytes, oral keratinocytes, organ culture cells, osteoblasts, ovarian tumour cells, pancreatic beta cells, pericytes, perineurial cells, root sheath cells, schwann cells, skeletal muscle cells, smooth muscle cells, sperm cells, stellate cells, synoviocytes, thyroid carcinoma cells, villous trophoblast cells, yolk sac carcinoma cells, oocytes, sperm or embryoid bodies; or any combination of the above.

In other embodiments, the cells are stem cells, for example, neural stem cells, adult stem cells, iPS cells or embryonic stem cells. In some preferred embodiments, the cells are blood cells, e.g. red blood cells, white blood cells or blood platelets.

In some particularly preferred embodiments, the cells are red blood cells which are substantially free from white blood cells and/or blood platelets. In some preferred embodiments, the cells are monolayers of cells.

The method applies, inter alia, to cells grown in both 2D and 3D tissue culture, and other ways.

In other embodiments, the biological material to be cryopreserved is in the form of a tissue or a whole organ or part of an organ. The tissues and/or organs and/or parts may or may not be submerged, bathed in or perfused with the composition prior to cryopreservation.

Examples of tissues include skin grafts, corneas, ova, germinal vesicles, or sections of arteries or veins. Examples of organs include the liver, heart, kidney, lung, spleen, pancreas, or parts or sections thereof. These may be of human or non-human (e.g. non-human mammalian) origin.

In some preferred embodiments, the biological material or cells are selected from semen, blood cells (e.g. donor blood cells or umbilical cord blood, preferably human), stem cells, tissue samples (e.g. from tumours and histological cross sections), skin grafts, oocytes (e.g. human oocytes), embryos (e.g. those that are 2, 4 or 8 cells when frozen), ovarian tissue (preferably human ovarian tissue) or plant seeds or shoots. The biological material may be living or dead (i.e. non-viable) material.

A further area in which the methods and compositions described herein find use is in food technology, specifically as texture modifiers for frozen food products.

Many frozen food products (including, but not limited to, ice cream, animal meat and fruit) suffer from the growth of ice during storage which can adversely affect the texture of the product. For example, ice cream with large crystals has a grainy texture which is unappealing, whereas meat and fruit products which have been frozen tend to lose significant volumes of water when defrosted due to ice-induced damage to the structure of the product.

Incorporation of the compositions described herein in any of these food products may be beneficial. When used in any food application, biocompatibility of the compositions is important, as well as solubility in any solution in which these may be applied to the product or in any formulation in which these may be provided.

In particular, the compositions which are described herein may be used to reduce or inhibit ice crystal growth in food products, for example during their production and/or storage in a frozen state (e.g. at a temperature of between −15° C. and −40° C.). Texture and flavour are typically adversely affected due to the formation of large ice crystals during the freeze-thaw cycle which takes place in most home freezers or on long term storage in the frozen state. This ice crystal growth can be minimised or even prevented entirely when using the compositions which are herein described. As a result, the texture, taste and useful storage life of frozen food products can be improved.

The compositions may be added to any food which is to be frozen until consumption or which may remain frozen during consumption and may either be incorporated throughout the entire product or, alternatively, applied only to the surface of the product which is where ice crystal growth occurs most readily. The composition may be added during conventional methods of food preparation and may be added prior to, during, or after freezing of the product. If added after freezing, this is done before the product is finally hardened so that the composition may be mixed into the product. For example, this may be incorporated into frozen foods which are intended to be consumed in the frozen state such as ice creams, frozen yoghurts, sorbets, frozen puddings, ice lollies, etc. whereby to improve mouth-feel due to the lack of large crystal formation during preparation and storage. Typically, the composition will be mixed with other ingredients during the manufacture of the products.

Other frozen food products which may benefit from the invention include frozen fruit and vegetables, such as strawberries, raspberries, blueberries, citrus fruits, pineapples, grapes, cherries, plums, peas, carrots, beans, sweetcorn, broccoli, spinach, etc.

Frozen food products which incorporate the compositions herein described and which are intended to be consumed in the frozen state and/or stored in the frozen state form a further aspect of the invention.

Preferred food products include ice cream and sorbets which will include other ingredients conventionally found in such products, such as fats, oils, sugars, thickeners, stabilisers, emulsifiers, colourings, flavourings and preservatives. In such products, the total amount of the composition will typically be at least about 0.01 wt. %, preferably at least 0.1 wt. %, e.g. about 0.5 wt. %. Ideal concentrations can be readily determined by those skilled in the art in the knowledge that this should be used at as low a concentration as possible whilst still having the desired effect of preventing ice re-crystallisation.

As used herein, the term "treating the substance" includes, inter alia, immersing or submerging the substance in the composition or infusing or perfusing the substance with the composition such that the composition makes intimate contact with all or substantially all of the parts of the substance.

In embodiments wherein the substance is a food product, such as ice cream, the composition may be mixed with the food product.

In general, the substance will be treated with the composition prior to and/or during cryopreservation. Preferably, the substance is treated prior to cryopreservation. In some embodiments, the substance may be cryopreserved in the composition. In other embodiments, the substance is already cryopreserved (i.e. at a cryopreserving temperature) before it is treated with the composition.

As used herein, the terms "cryopreserving" and "cryopreservation" refer to the storage of the substance, e.g. cells, tissues or organs, at temperatures below 4° C.

In the context of biological material, the intention of the cryopreservation is to maintain the biological material in a preserved or dormant state, after which time the biological material is returned to a temperature above 4° C. for subsequent use.

Preferably, the cryopreserving temperature is below 0° C. For example, the cryopreserving temperature may be below −5° C., −10° C., −20° C., −60° C. or in liquid nitrogen or liquid helium, carbon dioxide ('dry-ice'), or slurries of carbon dioxide with other solvents. In some preferred embodiments, the cryopreserving temperature is about −20° C., about −80° C. or about −180° C.

The method of the invention may additionally comprise the step of cryopreserving or freezing the substance. The cryopreserving or freezing of the substance may take place in the composition or before the substance is contacted with or placed in the composition. In other words, the substance may be frozen before it is contacted with the composition. As used herein, the term "freezing" or "frozen" refers to reducing the temperature to a cryopreserving temperature or being at a cryopreserving temperature.

In general, the substance will be placed in the composition and then the temperature will be reduced. It may be reduced directly to the final cryopreserving temperature or first to an intermediate temperature (which may be above or below the final cryopreserving temperature).

The rate of the freezing step may, for example, be slow (e.g. 1-10° C./minute), or fast (above 10° C./min). In some embodiments, the rate of freezing is at least 10° C./minute, preferably at least 20° C./minute, at least 50° C./minute or at least 100° C./minute. In some embodiments, the rate of freezing is between 10° C./minute and 1000° C./minute, between 10° C./minute and 500° C./minute, or between 10° C./minute and 100° C./minute.

Fast rates of freezing may induce the production of ice crystals in the composition. Crystals produced in this way are small; they are also generally numerous. Upon warming or thawing of the cryopreserved composition, it has been found that the presence of poly(proline) in the composition inhibits the natural recrystallisation of these small ice crystals into larger ones, thus significantly reducing the cell death in biological material which would normally occur at this time.

The most preferred freezing rate in any one particular case will be dependent on the volume of the composition and the nature of the substance. By following the teachings herein and the above points in particular, the skilled person may readily determine the most appropriate freezing rate in any one case.

In general, the substance will initially be at a temperature about 0° C., e.g. at about 4° C. or at ambient temperature. From there, its temperature will be reduced to the cryopreserving temperature, preferably in a single, essentially uniform step (i.e. without a significant break).

Rapid freezing using solid $CO_2$ slurries or liquid $N_2$ are preferred, which cool at approximately 100° C./min. It is also possible to achieve similar rates using other cryogens which have a temperature which is colder than standard refrigerators (e.g. below −20° C.).

Preferably, the substance or composition comprising the substance is not stirred and/or is not agitated during the freezing step.

The method of the invention may additionally comprise the step of warming or thawing the cryopreserved substance. In some embodiments, the term "thawing" refers to raising the temperature of the cryopreserved substance (e.g. biological material) to 0° C. or above, preferably to 4° C. or above. In other embodiments, the term "thawing" refers to raising the temperature of the cryopreserved substance to a temperature at which there are no or substantially no ice crystals in all or part of the cryopreserved substance. Hence the term "thawing" includes complete and partial thawing.

The substance may subsequently be isolated or removed from the composition.

The term "recrystallization" is known in the context of cryopreservation to refer to the growth of existing ice crystals during the warming or thawing or a cryopreserved substance or product.

The term "recrystallization" may be contrasted with the term "nucleation" which relates to the formation of new ice crystals.

The rate of thawing may, for example, be slow (e.g. 1-10° C./minute) or fast (above 10° C./min). In some cases it may be advantageous to thaw slowly. Rapid thawing in a water bath at 37° C. is preferred. Cell recovery is also possible at lower temperatures (e.g. 20° C.).

Alternatively, the temperature of the cryopreserved substance may be raised to a temperature at which the cryopreserved substance may be removed from or isolated from the composition (e.g. 4° C. or above); and the substance may then be stored at this temperature until use.

The invention therefore provides a method as described herein, wherein ice is present in the cryopreserved substance at one or more stages during thawing of the cryopreserved substance.

Ice nucleation within the cryopreserved substance may be tested for by differential scanning calorimetry or cryomicroscopy.

In some embodiments, the substance is cryopreserved at a rate which induces the production of ice crystals, most preferably small ice crystals, in the cryopreserved substance. As used herein, the term "small ice crystals" means that the ice crystals are less than 100 μm in length, more preferably less than 50 μm in length, and most preferably less than 25 μm, less than 20 μm, less than 10 μm or less than 5 μm in length. Length refers to the longest dimension of the ice crystal. Preferably, at least 80% of the ice crystals in the cryopreserved substance are less than 50 μm in length. Most preferably, at least 90% of the ice crystals in the cryopreserved substance are less than 20 μm in length. Most preferably, at least 95% of the ice crystals in the cryopreserved substance are less than 10 μm or less than 5 μm in length. The percentages of ice crystals in the cryopreserved substance having less than a specified size may be determined by optical or electron microscopy.

Cryopreserved biological material may be stored for cell, tissue and/or organ banking. The cryopreserved substance may be stored at the cryopreserving temperature for any desired amount of time. Preferably, it is stored for at least one day, at least one week or at least one year. More preferably, it is stored for 1-50 days, 1-12 months or 1-4 years. In some embodiments, it is stored for less than 5 years.

After cryopreservation, biological material may be used for any suitable use, including human and veterinary uses. Such uses include for tissue engineering, gene therapy and cellular implantation.

Also provided is a method of the invention wherein the substance is a biological material which is or has been pretreated with a composition comprising proline (monomers) before it is treated with a composition comprising poly(proline), or a variant or derivative thereof. In such methods, proline increases cell viability. Preferably, the biological material is pretreated with proline for 12-36 hours, more preferably about 24 hours.

The concentration of proline is preferably selected so as to help maintain the desired osmotic pressure within the cells of the biological material. In some embodiments it will be about 200 mM proline.

Preferably, the pre-treatment with proline is carried out in the absence of DMSO.

Homo-polypeptides can be prepared via solid-phase synthesis [31], solution-phase polymerization (N-carboxyanhydrides [32] or condensation) or by recombinant methods [33]. One example using solid-phase peptide synthesis is given in Example 1.

The invention further provides a kit comprising:
(i) poly(proline), or a variant or derivative thereof, and
(ii) instructions for use of the poly(proline) or a variant or derivative thereof in a method of the invention.

The kits may be used in the methods of the invention.

The invention also provides a cryopreserved biological material, wherein the cryopreserved biological material has been treated with poly(proline) or a variant or derivative thereof. Preferably, the cryopreserved biological material has been infused, perfused or admixed with poly(proline) or a variant or derivative thereof.

The invention also provides a frozen food product, wherein the frozen food product has been treated with poly(proline) or a variant or derivative thereof. Preferably, the frozen food product has been infused, perfused or admixed with poly(proline) or a variant or derivative thereof.

Preferably, the frozen food product comprises ice cream, meat, a fruit or a vegetable.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Data were analysed with a one-way analysis of variance (ANOVA) on ranks followed by comparison of experimental groups with the appropriate control group (Holm-Sidak method) followed by Tukey's post hoc test. Excel 2013 (Microsoft, Redmond, Wash.) and R (R Foundation for Statistical Computing, Vienna, Austria) were used for the analyses. Data sets are presented as mean±(SEM).

Example 1: Synthesis and Characterization of Poly(Proline)

Figure 1:
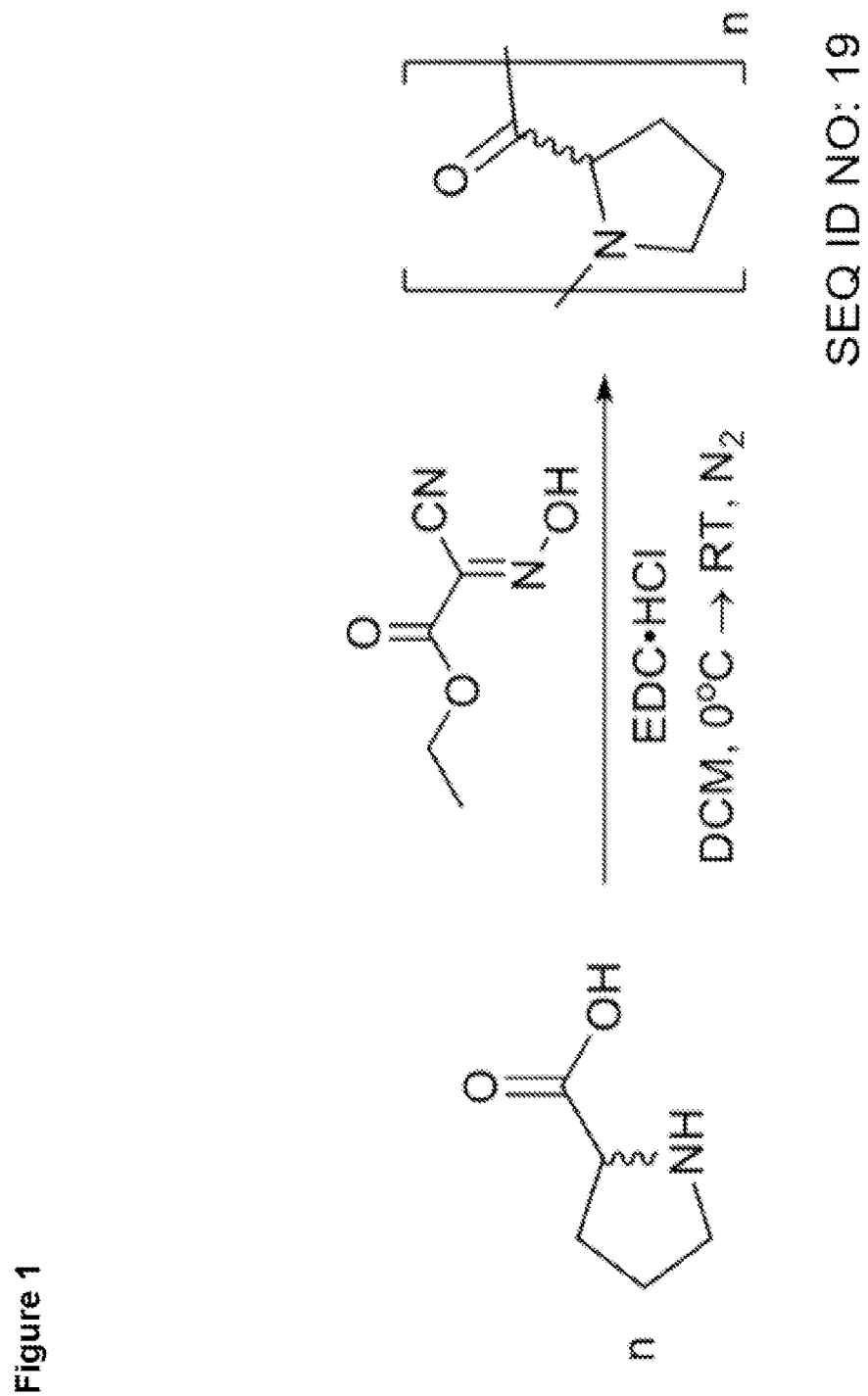
FIG. 1: Condensation polymerization of proline.
Figure 2A:
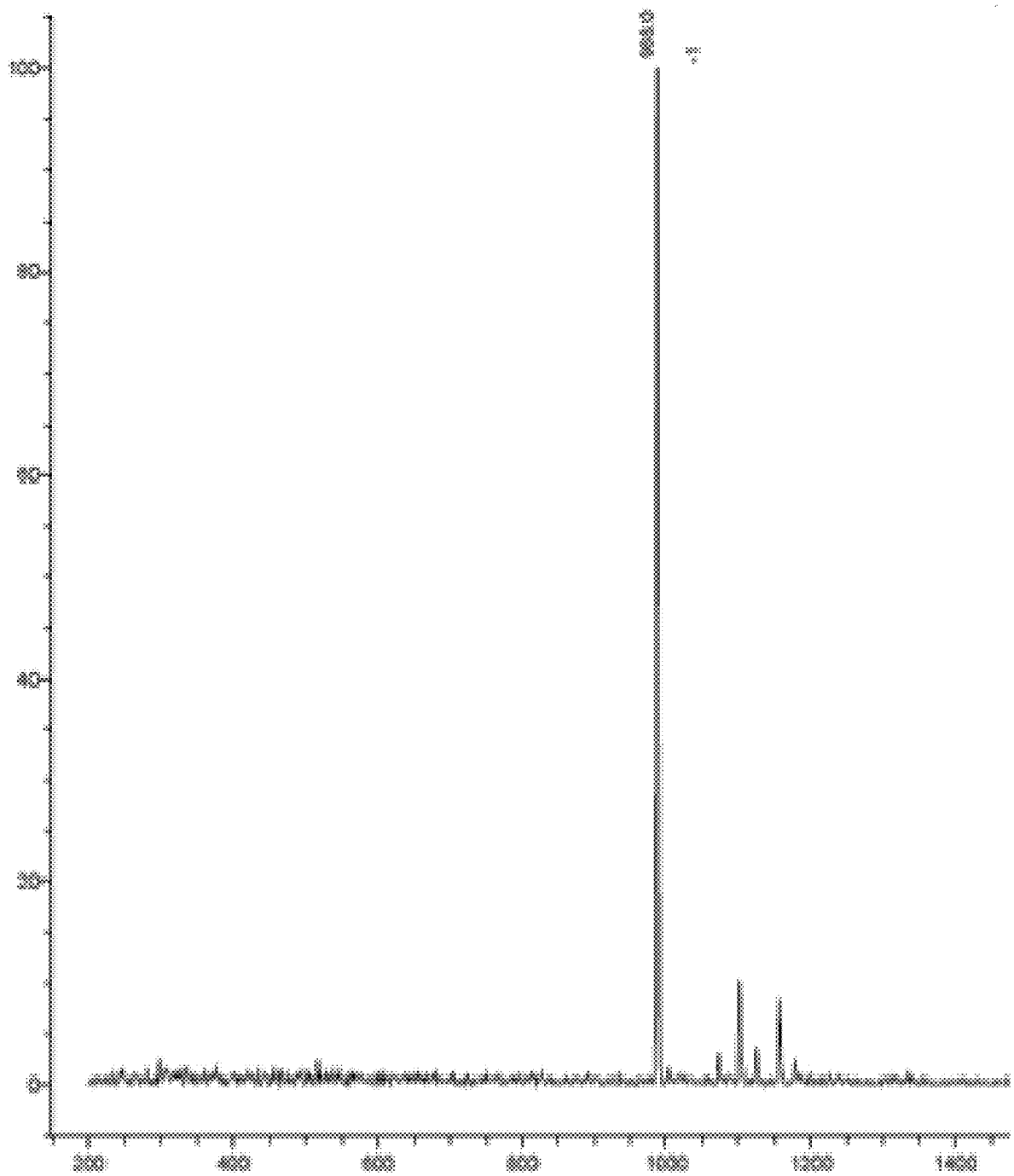
FIG. 2: ESI Mass Spec. A) PPro$_{10}$ (SEQ ID NO: 9). B) PPro$_{20}$ (SEQ ID NO: 13).
Figure 2B:
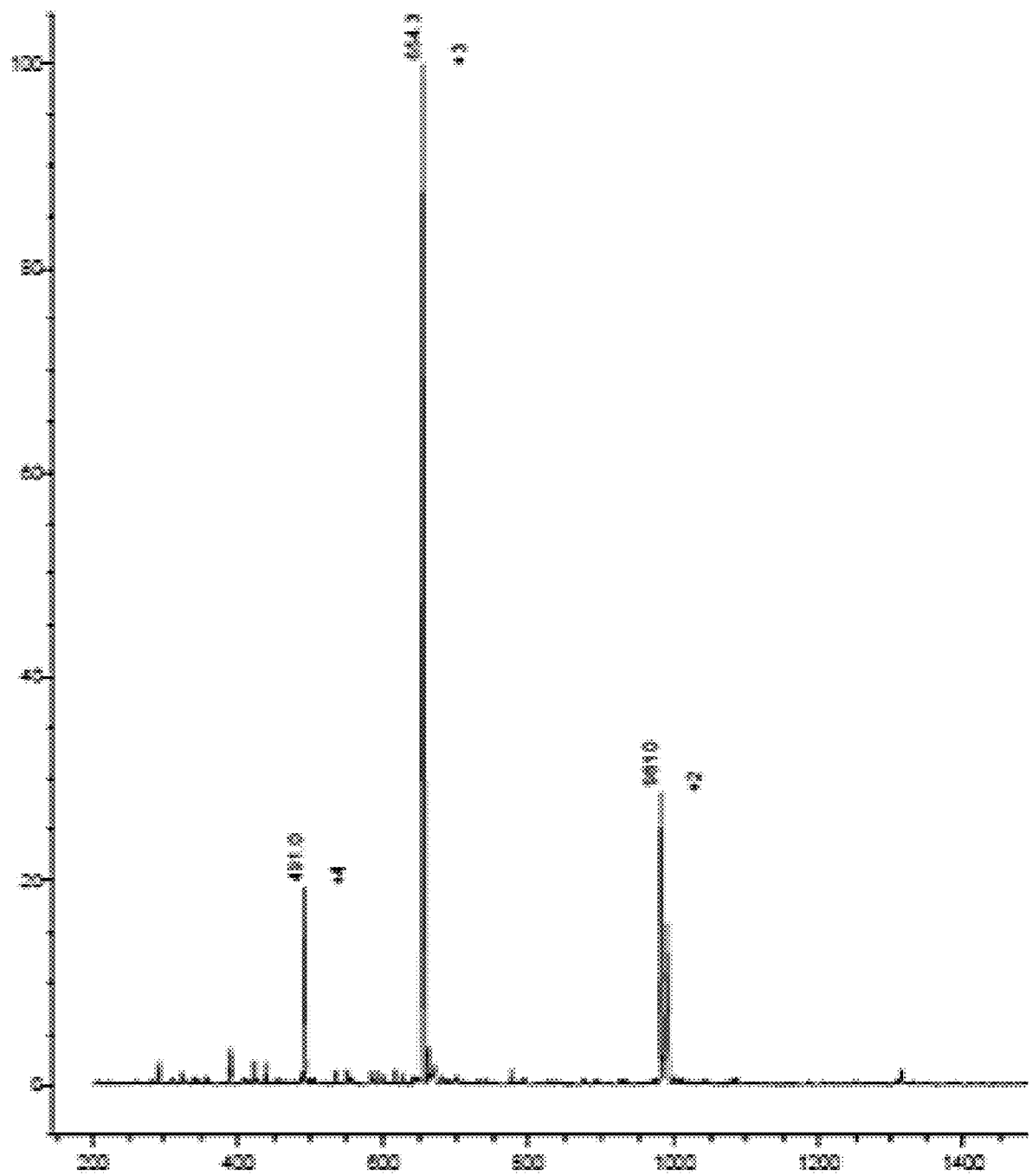

To obtain polyproline of different molecular weights, a range of synthetic methods were employed. Oligo-proline of DP 10 (PPro$_{10}$ (SEQ ID NO: 9)) and DP (PPro$_{20}$ (SEQ ID NO: 13)) were prepared by solid-phase peptide synthesis, alongside a high molecular weight commercial sample. L, D, and D/L (racemic) polyproline were synthesized by condensation polymerization using 1-ethyl-3-(3-dimethylaminopropyl) carbodiimide (EDC, FIG. 1). Following dialysis to remove excess amino acids, coupling reagents and low molecular weight fractions, the polymers were characterized by SEC (size exclusion chromatography) and the results shown in Table 1. This indicated molecular weights in the region of ~3000 g·mol$^{-1}$ and less disperse than expected due to fractionation during dialysis, and the rigid-rod like nature of the PPII helix which affects its SEC behaviour. Table 1 also contains polymers from previous work, which are included for later critical IRI activity analysis (vide infra).

TABLE 1

Poly(proline) characterization.

| | $M_n$, (g·mol$^{-1}$) | Ð,$^{SECa}$ (-) | DP (-) | Secondary Structure |
|---|---|---|---|---|
| PPro$_{11}$ (SEQ ID NO: 10) | 1300$^a$ | 1.03 | 11 | |
| PPro$_{15}$ (SEQ ID NO: 11) | 1700$^a$ | 2.12 | 15 | PPII |
| PPro$_{19}$ (SEQ ID NO: 12) | 2100$^a$ | 1.50 | 19 | |
| P(D)Pro$_{15}$ (SEQ ID NO: 11) | 1700$^a$ | 1.01 | 15 | Enantiomeric PPII |
| P(DL)Pro$_{21}$ (SEQ ID NO: 14) | 2400$^a$ | 1.01 | 21 | — |
| PPro$_{10-100}$ (SEQ ID NO: 4) | 1-10k$^b$ | — | 10-100 | PPII$^e$ |
| PPro$_{10}$ (SEQ ID NO: 9) | 900$^c$ | $^d$ | 10 | PPII$^e$ |
| PPro$_{20}$ (SEQ ID NO: 13) | 2000$^c$ | $^d$ | 20 | PPII$^e$ |

$^a$Determined by SEC;
$^b$Value from supplier;
$^c$Mass Spectrometry;
$^d$Single species
$^e$From Literature [34, 35 36].

Figure 3A:
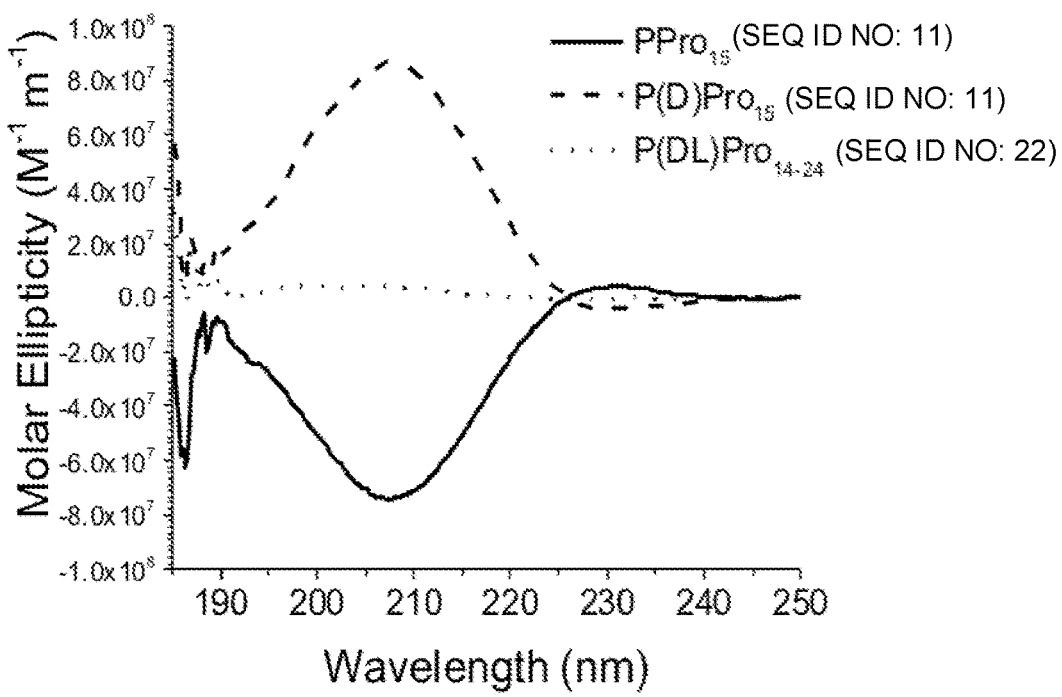
FIG. 3: Polyproline structure and activity. A) Circular dichroism spectra; B) IRI activity of polyproline series; C) IRI activity compared to other homo-polypeptides; D) Cryomicrograph of a PBS negative control; E) Cryomicrograph of 20 mg·mL$^{-1}$ polyproline. Photos taken after 30 mins at −8° C. Error bars represent ±standard deviation from minimum of 3 replicates. Images shown are 1.2 mm across. MLGS (mean largest grain size; F) Circular dichroism spectra. Synthesised proline polypeptides compared to a polyproline II helical reference (PPro (II) Helix) [37] not corrected for concentration to enable comparison against reference standard; G) SPLAT assay PBS control (× 200); H) SPLAT assay L-proline, 20 mg·mL$^{-1}$ (×200).

Circular dichroism spectroscopy (CD) confirmed that PPro$_{15}$ (SEQ ID NO: 11) adopted a PPII helix (FIG. 3A), compared to a standard (ESI, FIG. 3F) [37]. PPII (in CD) can be confused with a random coil. However, the characteristic signals associated with a PPII helix are present at 207 and 228 nm, whilst a random conformation exhibits slight peak shifting, with signals absent in the 220 nm region [38]. P(D)Pro$_{15}$ (SEQ ID NO: 11) gave the mirror spectrum as expected for D-amino acids, whilst the D/L racemic mixture showed essentially no secondary structure.

L- and D-proline, poly-L-proline mol wt 1,000-10,000 (PPro$_{10-100}$ (SEQ ID NO: 4)), ethyl (hydroxyimino) cyanoacetate (OxymaPure™), N-(3-dimethylaminopropyl)-N'-ethylcarbodiimide hydrochloride (EDCI), dichloromethane (DCM), phosphate-buffered saline preformulated tablets, and hydrochloric acid (37%) were purchased from Sigma Aldrich Co. Ltd. (Gillingham, UK) and used without further purification. Dialysis Membrane Spectra/Por 7 Flexible 38 mm FWT 1000 MWCO 4.6 mL/cm was purchased from Fischer Scientific (Loughborough, UK) and used directly. Phosphate-buffered saline (PBS) solution was prepared using preformulated tablets in 200 mL of Milli-Q water (>18.2Ω mean resistivity) to give [NaCl]=0.138 M, [KCl]=0.0027 M, and pH 7.4. PPro$_{10}$ (SEQ ID NO: 9) and PPro$_{20}$ (SEQ ID NO: 13) (>90%) were purchased bespoke from Peptide Protein Research Ltd (Fareham, UK) and were used without further purification. PPro$_{10}$ (SEQ ID NO: 9): m/z (ESI) 988.0 (100%, −1); PPro$_{20}$ (SEQ ID NO: 13): m/z (ESI) 491.0 (20%, +4), 654.3 (100%, +3), 981.0 (30%, +2).

SEC (size exclusion chromatography) was acquired a DMF Agilent 390-LC MDS instrument equipped with differential refractive index (DRI), viscometry (VS), dual angle light scatter (LS) and dual wavelength UV detectors. The system was equipped with 2×PLgel Mixed D columns (300×7.5 mm) and a PLgel 5 µm guard column. The eluent was DMF with 5 mmol NH4BF4 additive. Samples were run at 1 mL/min at 50° C. Poly(methyl methacrylate) standards (Agilent EasyVials) were used for calibration. Analyte samples were filtered through a nylon membrane with 0.22 µm pore size before injection. Respectively, experimental molar mass ($M_n$,SEC) and dispersity (Đ) values of synthesized polymers were determined by conventional calibration (relative to poly(methyl methacrylate) standards) using Agilent GPC/SEC software. Refractive index was recorded.

EDCI (0.50 g, 2.60 mmol) was dissolved in dry DCM (20 mL) and stirred at room temperature under a flow of nitrogen for 20 minutes, followed by cooling to 0° C. Within 5 minutes of cooling, L-proline (0.30 g, 2.60 mmol, 1 eqv) and OxymaPure™ (0.37 g, 2.60 mmol, 1 eqv) were added together to the reaction mixture, resulting in an instantaneous colour change to yellow. The mixture was stirred on ice under nitrogen for 1 further hour, and then warmed to RT with stirring overnight. The dark yellow solution was condensed in vacuo, dissolved in Milli-Q water (10 mL) acidified to pH 3-4 with 3M HCl, and a minimum volume of methanol added until residual solids dissolved. Dialysis (>1 kDa) for 48 hours was subsequently performed with regular water changes. The resulting solution was freeze dried, yielding an off-white solid. 31.4 mg (10.4%). The DL racemate, P(DL)Pro$_n$ (SEQ ID NO: 19), utilised a 1:1 ratio of L- and D-proline (2.60 mmol prolines).

Example 2: Ice Recrystallization Inhibition (IRI) Activity of Poly(Proline)

Figure 3B:
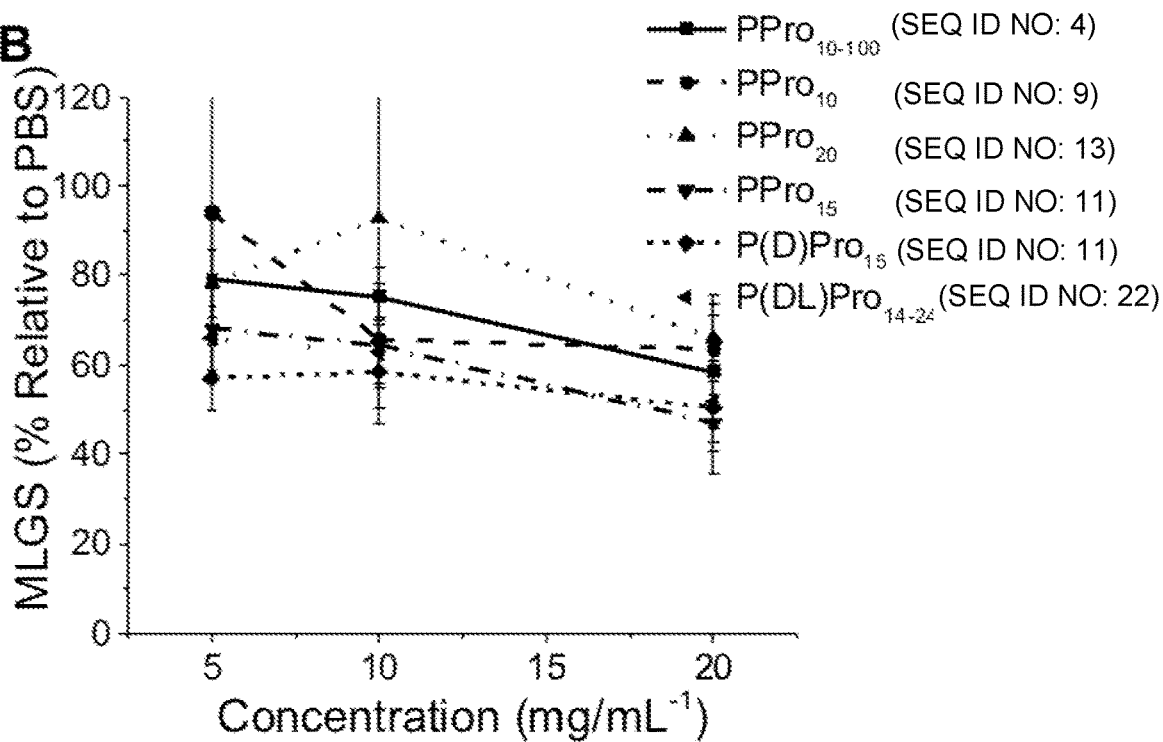

A series of peptides were tested for IRI activity using a SPLAT assay [39]. Briefly, this involved seeding a large number of small ice crystals, which were annealed for 30 minutes at −8° C., before being photographed. The average crystal size was then measured, relative to a PBS control, with smaller values indicating more IRI activity, FIGS. 3B/1C.

All peptides displayed a dose-dependent activity relationship with grain size reducing as concentration increased. Only weak molecular weight dependence was observed in the range tested. Example micrographs of a PPro$_{10-100}$ (SEQ ID NO: 4) ice wafer compared to a PBS control are shown in FIGS. 3D/1E, demonstrating potent inhibition. This activity was unexpected as most synthetic macromolecules show little or no IRI [15, 22, 40]. The shortest peptides (PPro$_{10}$ (SEQ ID NO: 9)) lost activity below 10 mg·mL$^{-1}$, but the longer polymers retained activity down to 5 mg·mL$^{-1}$. The magnitude of this activity is significantly weaker than AF(G)Ps which function at concentrations as low as 0.14 μg·mL$^{-1}$[41], but comparable to polyampholytes which have found application in cellular cryopreservation [22-23].

Ice recrystallisation inhibition (IRI) activity was measured using a modified splat assay [50]. A 10 μL sample of polymer dissolved in PBS buffer (pH 7.4) was dropped 1.40 m onto a chilled glass coverslip, resting on a thin aluminium block placed on dry ice. Upon hitting the coverslip, a wafer with diameter of approximately 10 mm and thickness 10 μm was formed instantaneously. The glass coverslip was transferred onto the Linkam cryostage and held at −8° C. under N$_2$ for 30 minutes. Photographs were obtained using an Olympus CX 41 microscope with a UIS-2 20 x/0.45/∞/0-2/FN22 lens and crossed polarizers (Olympus Ltd, Southend-on-Sea, UK), equipped with a Canon DSLR 500D digital camera. Images were taken of the initial wafer (to ensure that a polycrystalline sample had been obtained) and again after 30 minutes. Image processing was conducting using Image J, which is freely available. In brief, five of the largest ice crystals in the field of view were measured and the single largest length in any axis recorded. The average (mean) of these five measurements was then calculated to find the largest grain dimension along any axis. This was repeated for three individual wafers, and the average (mean) of these three values was calculated to give the mean largest grain size (MLGS). The average value was compared to that of a PBS buffer negative control.

Example 3: Effect of the PPII Helix on Ice Recrystallization Inhibition Activity Earlier work by Knight [42] observed that poly(hydroxyproline) had potent IRI activity, which was assumed to be due, in part, to the regularly spaced hydroxyl groups along the backbone. However, the observations made here suggest that it is the specific helical structure of poly(proline), rather than hydroxyl groups, which gives rise to the observed activity.

Figure 3C:
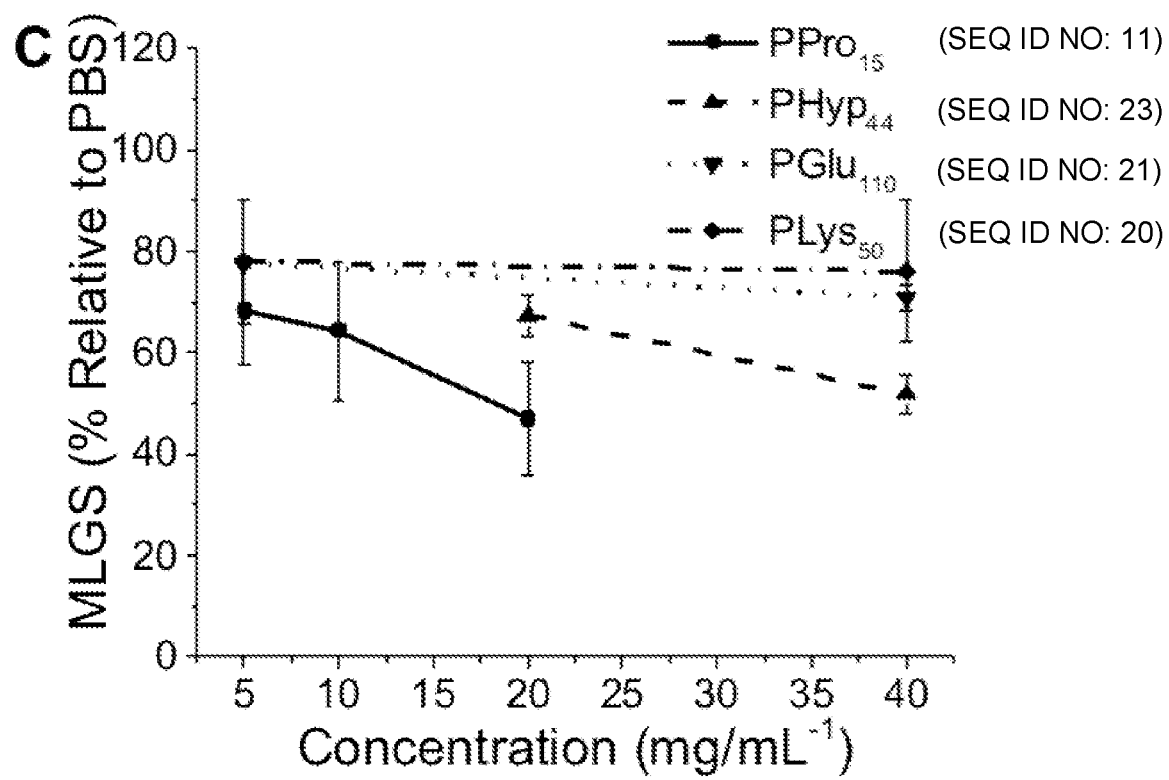
Figure 3D:
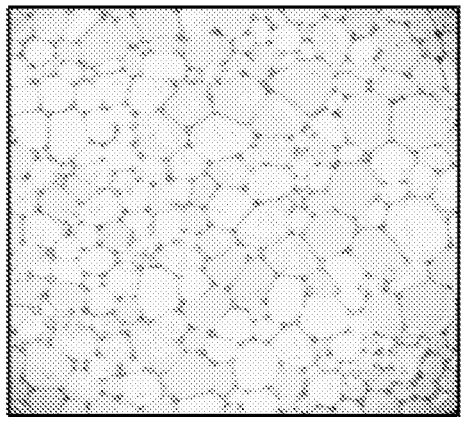
Figure 3E:
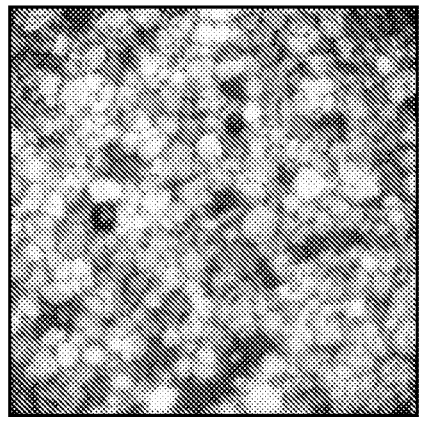

FIG. 3C shows a comparison of the IRI activity of poly(hydroxyproline) versus PPro$_{15}$ (SEQ ID NO: 11) and, two other alpha-helical poly(amino acids) [40]. These alpha-helical controls, poly(lysine) (PLys$_{50}$ (SEQ ID NO: 20)) and poly(glutamic acid) (PGlu$_{110}$ (SEQ ID NO: 21)), showed no IRI, similar to PEG, which was used as negative control.

P(D)Pro$_{15}$ (SEQ ID NO: 11) and P(DL)Pro$_{21}$ (SEQ ID NO: 14) had statistically identical activity to PPro$_{15}$ (SEQ ID NO: 11), ruling out any stereospecific effects. This may suggest that the local structure around the amide bond, and not the stereochemistry or folding, is crucial as opposed to long-range order (which may still have a contribution, however).

Example 4: Mapping of Hydrophobic/Hydrophilic Domains

Figures 4A, 4B, 4C:
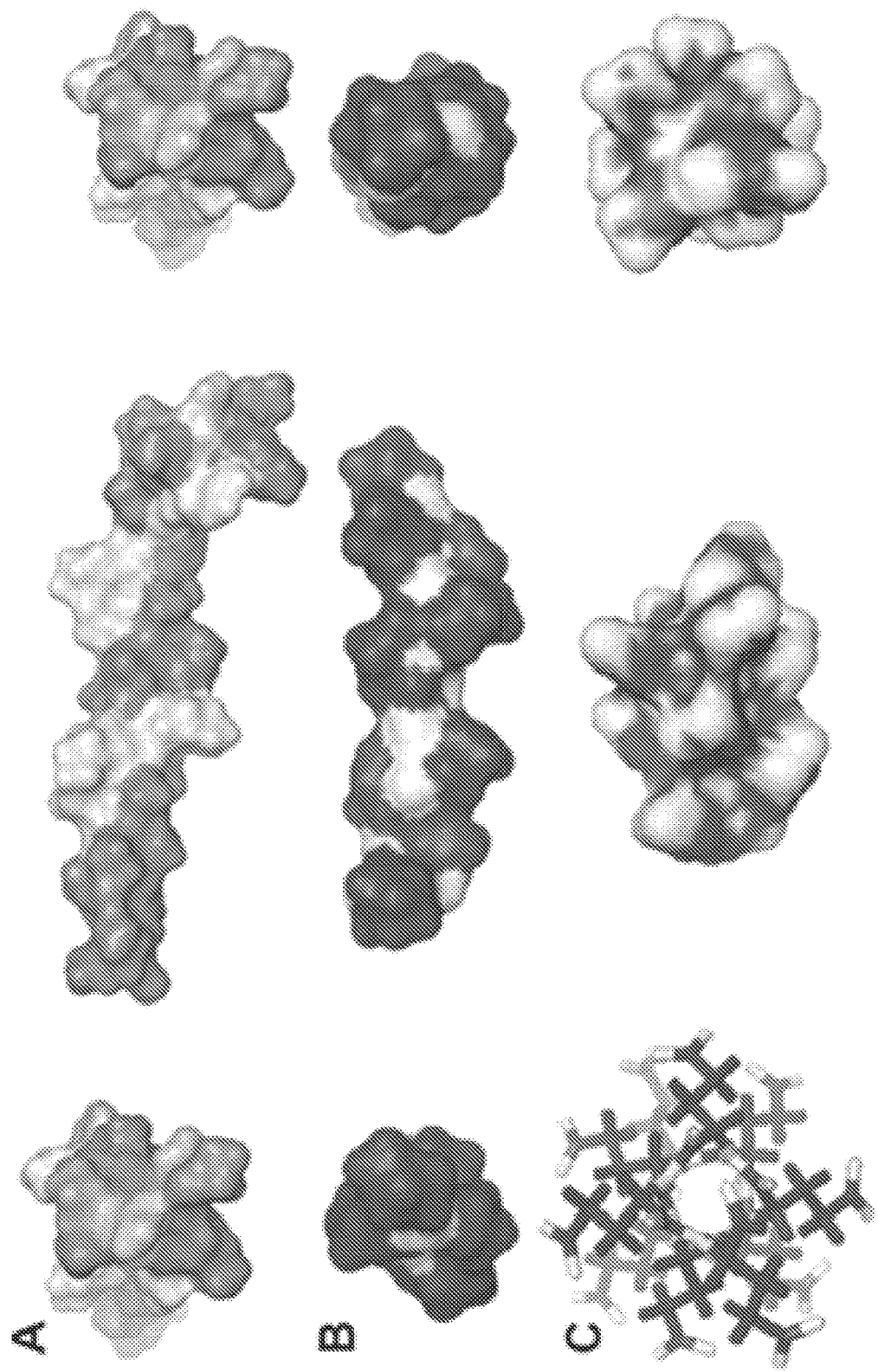
FIG. 4: Hydrophobic surface mapping of A) Recombinant Type I Sculpin AFP; B) PPro$_{10}$ (SEQ ID NO: 9); C) PGlu$_{10}$ (SEQ ID NO: 18) showing charged hydrophilic surface.

It is hypothesised that IRI activity requires a balance between hydrophilic and hydrophobic domains for activity (amphipathy) [25, 27]. PPro$_{10}$ (SEQ ID NO: 9) was compared to that of a non-glycosylated Type I sculpin antifreeze protein (AFP) [43] and also against PGlu$_{10}$ (SEQ ID NO: 18), by mapping their hydrophobic/hydrophilic domains (FIG. 4).

NMR solution phase (AFP Sculpin) and X-ray crystal structures of proteins and peptides of interest were acquired from the Protein Data Bank and other publically accessible sources, or computationally modelled in-house (PPro$_{10}$ (SEQ ID NO: 9) and PGlu$_{10}$ (SEQ ID NO: 18)). Structures were rendered in PyMOL (Schrödinger LLC, Cambridge, Mass.), which is freely available for educational use, and surfaces on the structures were displayed. An open source script "color_h" was used to colour the protein surface according to the Eisenberg hydrophobicity scale of its constituent amino acids, from red (hydrophobic) to white (hydrophilic). For the homo-polypeptides where scaling is not possible, aliphatic hydrogen and carbon were defined as hydrophobic whilst oxygen, hydrogen and nitrogen as hydrophilic, utilising the same colour scheme. Due to the lack of hydrogen bond donors in a PPro$_{10}$ (SEQ ID NO: 9) PPII helix, this was considered representative.

Type I sculpin AFP (FIG. 4A) clearly possesses a segregated domain structure with regular 'patches' of hydrophobic/hydrophilic groups. PPro$_{10}$ (SEQ ID NO: 9) (FIG. 4B) also possesses this facial amphiphilicity, with 'hydrophilic pockets' visible between the mostly hydrophobic polypeptide. In comparison, PGlu$_{10}$ (SEQ ID NO: 18) (FIG. 4C, no IRI activity) has charged hydrophilic groups protruding from around the core of the helix, which prevents the presentation of core hydrophobic domains. This agrees with our previous study on Nisin A, which has pH-dependent IRI associated with segregated domains [27] and also of amphiphiles developed by Capicciotti et al. [25], which only function below the CMC (critical micelle concentration) [25].

Example 5: Effect of Poly(Proline) on Cryopreservation of Cells

Figure 5A:
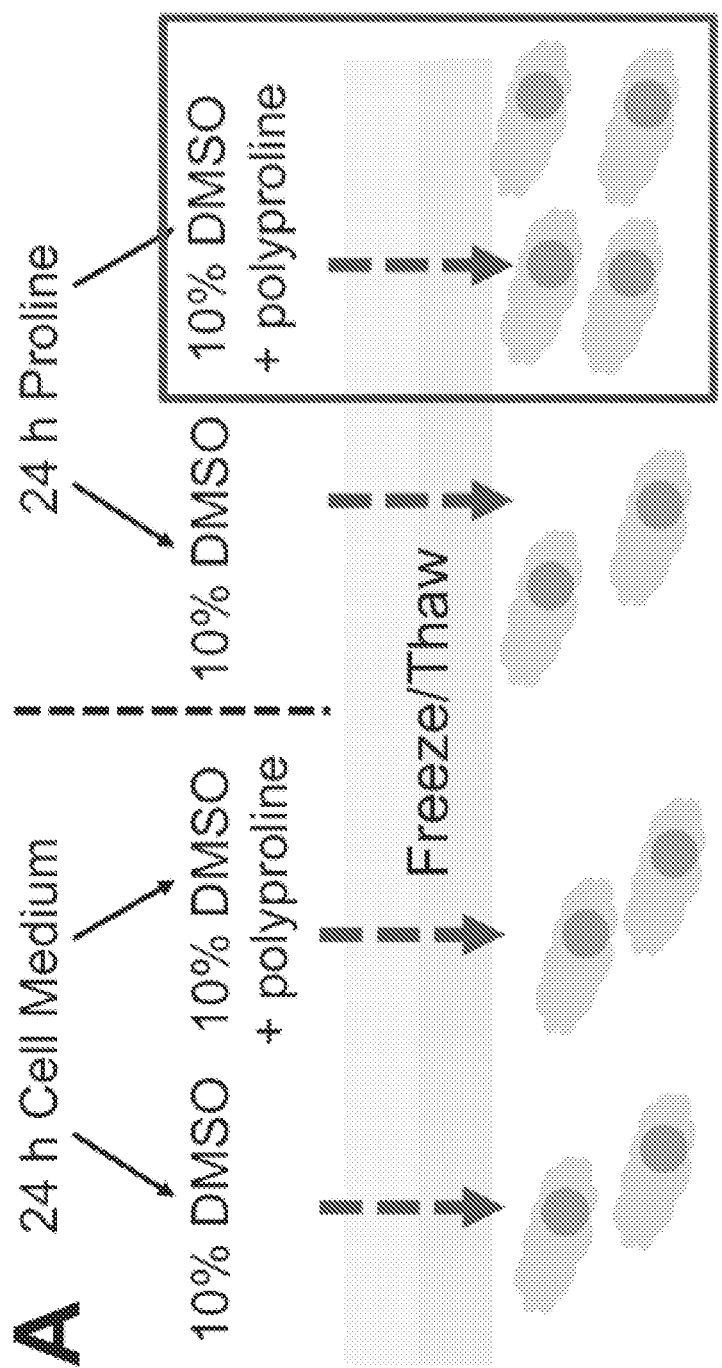
FIG. 5: A549 Cryopreservation. A) Schematic of procedures used; B) Cell recovery by trypan blue assay. Cells were incubated either in media alone or with 200 mM proline for 24 hours, then cryopreserved by addition of 10% DMSO with or without PPro$_{11}$ (SEQ ID NO: 10). Error bars±S.E.M. from n=3 with two nested replicates. (#P<0.05 compared to 10% DMSO treatment; * P<0.05 compared to 200 mM proline exposure with 10% DMSO treatment.

A549 (human Caucasian lung carcinoma) cells were employed as prototypical adherent cell monolayer which are challenging to cryopreserve by traditional methods [46]. Rather than traditional DMSO-only cryopreservation, the protective osmolyte proline (which has no IRI activity unlike the polymer—see ESI) was also added; proline accumulates under water stress in some organisms, and aids the cryopreservation process [47-48]. A549 cells were incubated with 200 mM (23 mg·mL$^{-1}$) proline or media alone for 24 hours. The solution was then removed and replaced with 10% DMSO with PPro$_{11}$ (SEQ ID NO: 10) (1250 g·mol$^{-1}$, Đ=1.03). After 10 minutes exposure, all excess solvent was removed, before controlled freezing at 1° C.·min$^{-1}$ to −80° C., FIG. 5A. Following storage at −80° C., cells were thawed by addition of warm media and the total number of viable cells assessed via trypan blue 24 hours post-thaw.

Figure 5B:
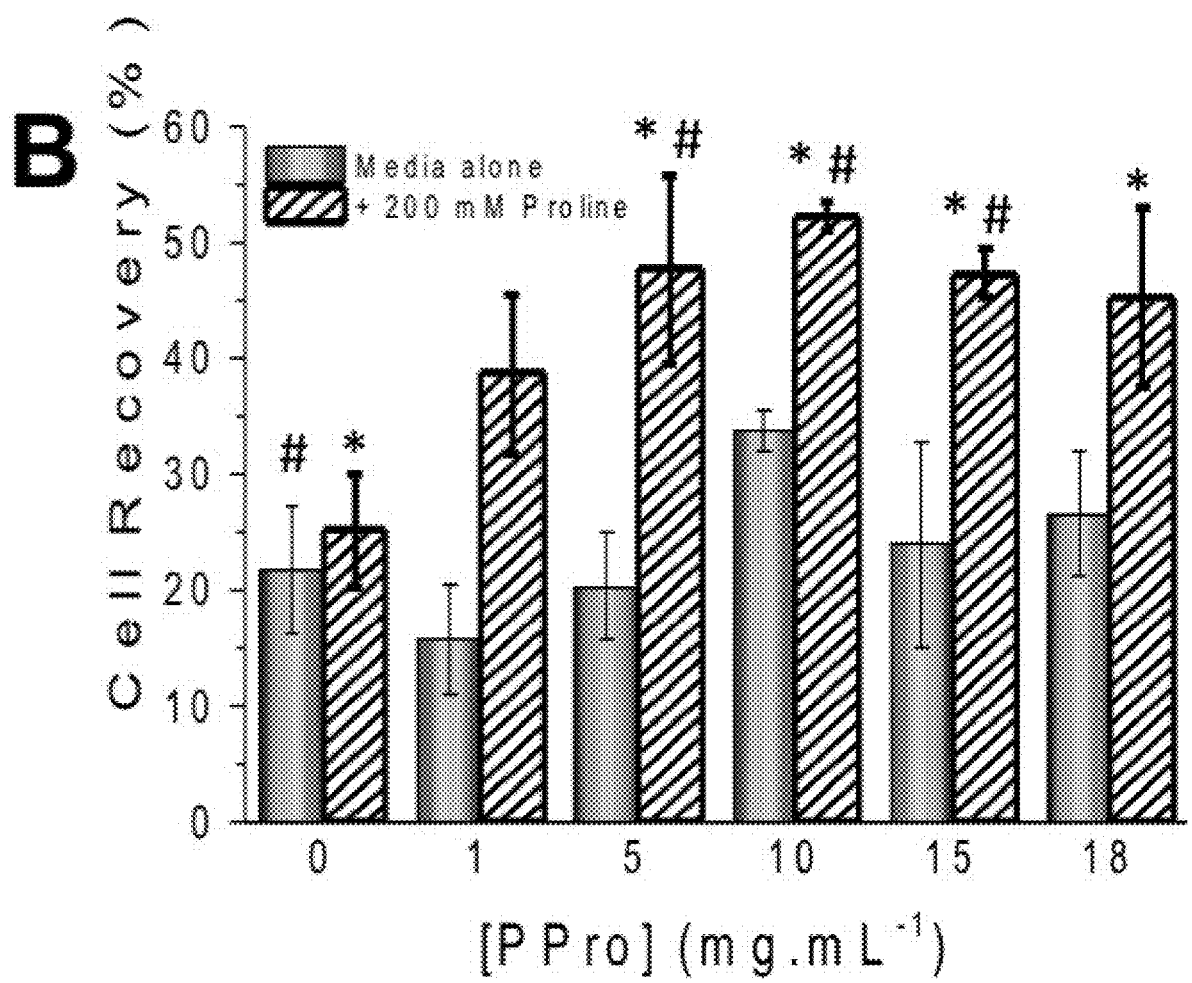

FIG. 5B shows that using DMSO, the current 'gold' standard for cryopreservation, lead to just 27% of the frozen cells being recovered. It was also observed that addition of poly(proline) to 10% DMSO also failed to give any additional protection. However, cells which had been pre-conditioned with 200 mM proline for 24 h then treated with 5 mg·mL$^{-1}$ PPro$_{11}$ (SEQ ID NO: 10) and 10% DMSO dramatically increased recovery of viable cells to 53%. Increasing the concentration of poly(proline) beyond 10 mg·mL$^{-1}$ did not increase recovery further, as reported for other IRI's [16]. This is an unprecedented improvement in recovery for a macromolecular antifreeze and demonstrated the successful, rational, design, characterisation and application of a simplistic antifreeze protein mimic.

Human Caucasian lung carcinoma cells (A549) were obtained from the European Collection of Authenticated Cell Cultures (Salisbury, UK) and grown in 175 cm$^2$ cell culture Nunc flasks (Corning Incorporated, Corning, N.Y., USA). Standard cell culture medium was composed of Ham's F-12K (Kaighn's) Medium (F-12K) (Gibco, Paisley, UK) supplemented with 10% USA-origin foetal bovine serum (FBS) purchased from Sigma Aldrich Co Ltd (Gillingham, UK), 100 units/mL penicillin, 100 µg/mL streptomycin, and 250 ng/mL amphotericin B (PSA) (HyClone, Cramlington, UK). A549 cells were maintained in a humidified atmosphere of 5% $CO_2$ and 95% air at 37° C. and the culture medium was renewed every 3-4 days. The cells were subcultured every 7 days or before reaching 90% confluency. To subculture, cells were dissociated using 0.25% trypsin plus 1 mM EDTA in balanced salt solution (Gibco) and reseeded at 1.87×10$^5$ cells per 175 cm$^2$ cell culture flasks.

Solutions for cell incubation experiments were prepared by dissolving the individual compounds in F-12K supplemented with 10% FBS and 1× PSA (solutions used as freezing buffers did not contain PSA) and sterile filtered prior to use.

Cells to be frozen in the monolayer format were seeded at 0.4×10$^6$ cells per well in 500 µL of cell culture medium in 24-well plates (Corning Incorporated, Corning, N.Y.). Plates had a total available volume of 3.4 mL with an approximate growth area of 1.9 cm$^2$, no coverslips were used and plates were used with the accompanying lid. Cells were allowed to attach to the entire free surface of the bottom of the well and formed a confluent layer not greater in height than one cell. Before experimental treatments, cells were allowed to attach for 2 h to the plates in a humidified atmosphere of 5% $CO_2$ and 95% air at 37° C. The medium was exchanged against medium that was or was not supplemented with solutes as indicated in the figure. Control cells received no additional solutes and experimental cells were incubated with 23.1 mg/mL L-proline for 24 h in a humidified atmosphere of 5% $CO_2$ and 95% air at 37° C. Following the incubation period, the culture medium was removed and cells were exposed for 10 min at room temperature to different concentrations of solutes dissolved in F-12K supplemented with 10% FBS and 10% DMSO. After 10 min, the freezing solutions were removed and the plates placed inside a CoolCell® MP plate (BioCision, LLC, Larkspur, Calif., USA), transferred to a −80° C. freezer and frozen at a rate of 1° C./min. After 24 h at −80° C., cells were rapidly thawed by addition of 500 µL cell culture medium warmed to 37° C. Cells were placed in a humidified atmosphere for 24 h and then dissociated using 0.25% trypsin plus 1 mM EDTA in balanced salt solution. The number of viable cells was then determined by counting with a haemocytometer (Sigma Aldrich Co. Ltd, UK) at room temperature after 1:1 dilution of the sample with 0.4% trypan blue solution (Sigma Aldrich Co. Ltd, UK). The initial cell medium was discarded such that any non-attached cells were not included in the assessment. The percentage of recovered cells was calculated by dividing the number of cells with intact membranes after freezing and thawing by the number of cells present prior to freezing (i.e. after application of pre-treatments), multiplied by 100.

REFERENCES

The disclosure of each reference set forth herein is specifically incorporated herein by reference in its entirety.
1. Fowler, A. & Toner, M. Cryo-injury and biopreservation. *Ann. N. Y. Acad. Sci.* 1066, 119-135 (2005).
2. Walsh, G. Biopharmaceutical benchmarks 2006. *Nat. Biotechnol.* 24, 769-76 (2006).
3. Seth, G. Freezing mammalian cells for production of biopharmaceuticals. *Methods* 56, 424-31 (2012).
4. Shu, Z., Heimfeld, S., Gao, D. & Hutchinson, F. HHS Public Access. 49, 469-476 (2015).
5. Brockbank, K. & Taylor, M. Cryopreservation: An emerging paradigm change. *Adv. biopreservation* 5, 157-196 (2007).
6. Iwatani, M. et al. Dimethyl sulfoxide has an impact on epigenetic profile in mouse embryoid body. *Stem Cells* 24, 2549-2556 (2006).
7. Kawai, K., Li, Y.-S., Song, M.-F. & Kasai, H. DNA methylation by dimethyl sulfoxide and methionine sulfoxide triggered by hydroxyl radical and implications for epigenetic modifications. *Bioorg. Med. Chem. Lett.* 20, 260-5 (2010).
8. Heng, B. C. et al. Loss of viability during freeze-thaw of intact and adherent human embryonic stem cells with conventional slow-cooling protocols is predominantly due to apoptosis rather than cellular necrosis. *J. Biomed. Sci.* 13, 433-445 (2006).
9. Xu, Q., Brecht, W. J., Weisgraber, K. H., Mahley, R. W. & Huang, Y. Apolipoprotein E4 domain interaction occurs in living neuronal cells as determined by fluorescence resonance energy transfer. *J. Biol. Chem.* 279, 25511-6 (2004).

10. Xu, X. et al. The roles of apoptotic pathways in the low recovery rate after cryopreservation of dissociated human embryonic stem cells. *Biotechnol. Prog.* 26, 827-837 (2010).
11. Mazur, P. Cryobiology: the freezing of biological systems. *Science* 168, 939-49 (1970).
12. Mazur, P., Farrant, J., Leibo, S. P. & Chu, E. H. Survival of hamster tissue culture cells after freezing and thawing. Interactions between protective solutes and cooling and warming rates. *Cryobiology* 6, 1-9 (1969).
13. Stephenne, X., Najimi, M. & Sokal, E. M. Hepatocyte cryopreservation: Is it time to change the strategy? *World J. Gastroenterol.* 16, 1-14 (2010).
14. Chao, H., Davies, P. L. & Carpenter, J. F. Effects of antifreeze proteins on red blood cell survival during cryopreservation. *J. Exp. Biol.* 199, 2071-2076 (1996).
15. Gibson, M. I. Slowing the growth of ice with synthetic macromolecules: beyond antifreeze(glyco) proteins. *Polym. Chem.* 1, 1141 (2010).
16. Deller, R. C., Vatish, M., Mitchell, D. A. & Gibson, M. I. Synthetic polymers enable non-vitreous cellular cryopreservation by reducing ice crystal growth during thawing. *Nat. Commun.* 5, 3244 (2014).
17. Wowk, B. et al. Vitrification enhancement by synthetic ice blocking agents. *Cryobiology* 40, 228-236 (2000).
18. Deller, R. C., Pessin, J. E., Vatish, M., Mitchell, D. A. & Gibson, M. I. Enhanced non-vitreous cryopreservation of immortalized and primary cells by ice-growth inhibiting polymers. *Biomater. Sci.* 47, 935-945 (2016).
19. Budke, C. & Koop, T. Ice recrystallization inhibition and molecular recognition of ice faces by poly(vinyl alcohol). *ChemPhysChem* 7, 2601-2606 (2006).
20. Matsumura, K. et al. Cryopreservation of a Two-dimensional Monolayer Using a Slow Vitrification Method with Polyampholyte to Inhibit Ice Crystal Formation. *ACS Biomater. Sci. Eng.* 1023-1029 (2016).
21. Matsumura, K. & Hyon, S. H. Polyampholytes as low toxic efficient cryoprotective agents with antifreeze protein properties. *Biomaterials* 30, 4842-4849 (2009).
22. Mitchell, D. E., Lilliman, M., Spain, S. G. & Gibson, M. I. Quantitative study on the antifreeze protein mimetic ice growth inhibition properties of poly(ampholytes) derived from vinyl-based polymers. *Biomater. Sci.* 2, 1787-1795 (2014).
23. Mitchell, D. E., Cameron, N. R. & Gibson, M. I. Rational, yet simple, design and synthesis of an antifreeze-protein inspired polymer for cellular cryopreservation. *Chem. Commun.* 51, 12977-80 (2015).
24. Geng, H. et al. Graphene Oxide Restricts Growth and Recrystallization of Ice Crystals Communications Angewandte. *Angew. Chem. Int. Ed.* 56, 997-1001 (2017).
25. Capicciotti, C. J. et al. Potent inhibition of ice recrystallization by low molecular weight carbohydrate-based surfactants and hydrogelators. *Chem. Sci.* 3, 1408-1416 (2012).
26. Tam, R. Y., Ferreira, S. S., Czechura, P., Chaytor, J. L. & Ben, R. N. Hydration Index # A Better Parameter for Explaining Small Molecule Hydration in Inhibition of Ice Recrystallization Hydration IndexsA Better Parameter for Explaining Small Molecule Hydration in Inhibition of Ice Recrystallization. *Electrochemistry* 17494-17501 (2008).
27. Mitchell, D. E. & Gibson, M. I. Latent Ice Recrystallization Inhibition Activity in Nonantifreeze Proteins: Ca2+-Activated Plant Lectins and Cation-Activated Antimicrobial Peptides. *Biomacromolecules* 16, 3411-3416 (2015).
28. Nguyen, D. H., Colvin, M. E., Yeh, Y., Feeney, R. E. & Fink, W. H. The dynamics, structure, and conformational free energy of proline-containing antifreeze glycoprotein. *Biophys. J.* 82, 2892-2905 (2002).
29. Lin, Y., Duman, J. G. & DeVries, A. L. Studies on the structure and activity of low molecular weight glycoproteins from an antarctic fish. *Biochem. Biophys. Res. Commun.* 46, 87-92 (1972).
30. Devries, A. L., Komatsu, S. K. & Feeney, R. E. Chemical and Physical Properties of Freezing Point-depressing Glycoproteins from Antarctic Fishes. *J. Biol. Chem.* 245, 2901-2908 (1970).
31. Merrifield, R. B. Solid Phase Peptide Synthesis. I. The Synthesis of. *J. Am. Chem. Soc.* 85, 2149 (1963).
32. Gibson, M. I. & Cameron, N. R. Experimentally facile controlled polymerization of N-carboxyanhydrides (NCAs), including O-benzyl-L-threonine NCA. *J. Polym. Sci. Part A Polym. Chem.* 47, 2882-2891 (2009).
33. Gutierrez, E. et al. eif5A promotes translation of polyproline motifs. *Mol. Cell* 51, 35-45 (2013).
34. Adzhubei, A. A., Sternberg, M. J. E. & Makarov, A. A. Polyproline-II helix in proteins: Structure and function. *J. Mol. Biol.* 425, 2100-2132 (2013).
35. Wilhelm, P., Lewandowski, B., Trapp, N. & Wennemers, H. A crystal structure of an oligoproline PPII-Helix, at last. *J. Am. Chem. Soc.* 136, 15829-15832 (2014).
36. Mikhonin, A. V, Myshakina, N. S., Bykov, S. V, Asher, S. A. & Pennsyl, V. UV Resonance Raman Determination of Polyproline II, Extended 2. 5 1-Helix, and -Sheet ψ Angle Energy Landscape in Poly-L-Lysine and Poly-L-Glutamic Acid. *J. Am. Chem. Soc.* 127, 7712-7720 (2005).
37. Protein Circular Dichroism Data Bank. CD0004553000 (2016).
38. Lopes, J. L. S., Miles, A. J., Whitmore, L. & Wallace, B. A. Distinct circular dichroism spectroscopic signatures of polyproline II and unordered secondary structures: Applications in secondary structure analyses. *Protein Sci.* 23, 1765-1772 (2014).
39. Congdon, T., Notman, R. & Gibson, M. I. Antifreeze (Glyco)protein mimetic behaviour of poly(vinyl alcohol): Detailed structure ice recrystallization inhibition activity study. *Biomacromolecules* 14, 1578-1586 (2013).
40. Gibson, M. I., Barker, C. A., Spain, S. G., Albertin, L. & Cameron, N. R. Inhibition of ice crystal growth by synthetic glycopolymers: Implications for the rational design of antifreeze glycoprotein mimics. *Biomacromolecules* 10, 328-333
41. Lui, S. et al. In vitro studies of antifreeze glycoprotein (AFGP) and a C-linked AFGP analogue. *Biomacromolecules* 8, 1456-1462 (2007).
42. Knight, C. A., Wen, D. & Laursen, R. A. Nonequilibrium antifreeze peptides and the recrystallization of ice. *Cryobiology* 32, 23-34 (1995).
43. Kwan, A. et al. Solution structure of a recombinant Type I antifreeze protein: the effects of supercooling and N-acetylation. *Biochemistry* 44, 1980-1988 (2005).
44. Marcellini, M., Noirjean, C., Dedovets, D., Maria, J. & Deville, S. Time-lapse, in situ imaging of ice crystal growth with confocal microscopy. *ACS Omega* 1, 1019-1026 (2016).
45. Marcellini, M., Noirjean, C., Dedovets, D., Maria, J. & Deville, S. Time-Lapse, in Situ Imaging of Ice Crystal Growth Using Confocal Microscopy. *ACS Omega* 1, 1019-1026 (2016).
46. Stokich, B. et al. Cryopreservation of hepatocyte (HepG2) cell monolayers: Impact of trehalose. *Cryobiology* 69, 281-290 (2014).

47. Ashraf, M. & Foolad, M. R. Roles of glycine betaine and proline in improving plant abiotic stress resistance. *Environ. Exp. Bot.* 59, 206-216 (2007).
48. Yoshiba, Y., Kiyosue, T., Nakashima, K., Yamaguchi-Shinozaki, K. & Shinozaki, K. Regulation of Levels of Proline as an Osmolyte in Plants under Water Stress. *Plant Cell Physiol.* 38, 1095-1102 (1997).
49. Czechura, P., Tam, R. Y., Dimitrijevic, E., Murphy, A. V. & Ben, R. N. The importance of hydration for inhibiting ice recrystallization with C-linked antifreeze glycoproteins. *J. Am. Chem. Soc.* 130, 2928-2929 (2008).
50. C. A. Knight, J. Jallett, A. L. DeVries, *Cryobiology*, 1988, 25, 55-60.

The invention claimed is:

1. A method of preventing or inhibiting ice recrystallization in a substance which is susceptible to ice crystal growth upon cryopreservation and/or warming or thawing therefrom, the method comprising the step:
   (i) treating the substance with a composition comprising poly(proline) or a variant or derivative thereof,
wherein the poly(proline) or a variant or derivative thereof is a homogeneous or heterogeneous mixture of polymers which consist substantially or exclusively of linear chains of proline residues, the polymers having the general structure:

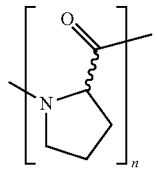

wherein n=3-200 (SEQ ID NO: 1); or 3-150 (SEQ ID NO: 2) or 5-100 (SEQ ID NO: 3); or 10-100 (SEQ ID NO: 4), 10-50 (SEQ ID NO: 5) or 10-25 (SEQ ID NO: 6); or 10-20 (SEQ ID NO: 7) or 11-15 (SEQ ID NO: 8).

2. A method of cryopreserving a substance which is susceptible to ice crystal growth upon cryopreservation and/or thawing or warming therefrom, the method comprising the steps:
   (i) treating the substance with a composition comprising poly(proline) or a variant or derivative thereof, wherein the poly(proline) or a variant or derivative thereof is as defined in claim 1;
   (ii) reducing the temperature of the treated substance to a cryopreserving temperature; and optionally
   (iii) storing the treated substance at the cryopreserving temperature.

3. A method of reducing cell damage during the warming or thawing of a cryopreserved substance comprising biological material, the method comprising the steps:
   (i) warming or thawing the cryopreserved substance comprising biological material,
wherein the cryopreserved substance is one which has been treated with poly(proline) or a variant or derivative thereof and wherein the poly(proline) or a variant or derivative thereof is as defined in claim 1.

4. The method of claim 1, wherein the substance is treated with poly(proline), or a variant or derivative thereof, before or during cryopreservation.

5. The method of claim 1, wherein the concentration of the poly(proline) or a variant or derivative thereof in the composition is 1-50 mg/mL, or 10-40, 10-30 or 10-20 mg/mL.

6. The method of claim 1, wherein the composition is a cryopreserving composition comprising DMSO.

7. The method of claim 1, wherein the substance is a biological material or a food product.

8. The method of claim 7, wherein the biological material comprises one or more of cells, tissues, whole organs and parts of organs.

9. The method of claim 8, wherein the cells are bacterial cells, fungal cells, plant cells, animal cells, mammalian cells, or human cells.

10. The method of claim 8, wherein the cells are monolayers of cells.

11. The method of claim 7, wherein the biological material is pretreated with proline prior to treatment with poly (proline) or a variant or derivative thereof.

12. The method of claim 7, wherein the food product comprises ice cream, sorbet, animal meat, a vegetable or a fruit.

13. The method of claim 2, wherein the concentration of the poly(proline) or a variant or derivative thereof in the composition is 1-50 mg/mL, or 10-40, 10-30 or 10-20 mg/mL.

14. The method of claim 3, wherein the concentration of the poly(proline) or a variant or derivative thereof in the composition is 1-50 mg/mL, or 10-40, 10-30 or 10-20 mg/mL.

15. The method of claim 2, wherein the composition is a cryopreserving composition comprising DMSO.

16. The method of claim 3, wherein the composition is a cryopreserving composition comprising DMSO.

17. The method of claim 2, wherein the substance is a biological material or a food product.

* * * * *

SEQUENCE LISTING

```
<160> NUMBER OF SEQ ID NOS: 23

<210> SEQ ID NO 1
<211> LENGTH: 3
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (3)..(3)
<223> OTHER INFORMATION: where Xaa = 1-198 proline residues

<400> SEQUENCE: 1

Pro Pro Xaa
1

<210> SEQ ID NO 2
<211> LENGTH: 3
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (3)..(3)
<223> OTHER INFORMATION: where Xaa = 1-148 proline residues

<400> SEQUENCE: 2

Pro Pro Xaa
1

<210> SEQ ID NO 3
<211> LENGTH: 5
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (5)..(5)
<223> OTHER INFORMATION: where Xaa = 1-96 proline residues

<400> SEQUENCE: 3

Pro Pro Pro Pro Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (10)..(10)
<223> OTHER INFORMATION: where Xaa = 1-91 proline residues

<400> SEQUENCE: 4

Pro Pro Pro Pro Pro Pro Pro Pro Pro Xaa
1               5                   10
```

```
<210> SEQ ID NO 5
<211> LENGTH: 10
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (10)..(10)
<223> OTHER INFORMATION: where Xaa = 1-41 proline residues

<400> SEQUENCE: 5

Pro Pro Pro Pro Pro Pro Pro Pro Pro Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (10)..(10)
<223> OTHER INFORMATION: where Xaa = 1-16 proline residues

<400> SEQUENCE: 6

Pro Pro Pro Pro Pro Pro Pro Pro Pro Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (10)..(10)
<223> OTHER INFORMATION: where Xaa = 1-11 proline residues

<400> SEQUENCE: 7

Pro Pro Pro Pro Pro Pro Pro Pro Pro Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (11)..(11)
<223> OTHER INFORMATION: where Xaa = 1-5 proline residues

<400> SEQUENCE: 8

Pro Pro Pro Pro Pro Pro Pro Pro Pro Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Poly(proline) with 10 proline residues

<400> SEQUENCE: 9

Pro Pro Pro Pro Pro Pro Pro Pro Pro Pro
```

1               5                   10

<210> SEQ ID NO 10
<211> LENGTH: 11
<212> TYPE: PRT
<213> ORGANISM: Artificial Sequence
<220> FEATURE:
<223> OTHER INFORMATION: Poly(proline) with 11 proline residues

<400> SEQUENCE: 10

Pro Pro Pro Pro Pro Pro Pro Pro Pro Pro Pro
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Poly(proline) with 15 proline residues

<400> SEQUENCE: 11

Pro Pro Pro Pro Pro Pro Pro Pro Pro Pro Pro Pro Pro Pro Pro
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: Poly(proline) with 19 proline residues

<400> SEQUENCE: 12

Pro Pro Pro Pro Pro Pro Pro Pro Pro Pro Pro Pro Pro Pro Pro Pro
1               5                   10                  15

Pro Pro Pro

<210> SEQ ID NO 13
<211> LENGTH: 20
<212> TYPE: PRT
<213> ORGANISM: Artificial Sequence
<220> FEATURE:
<223> OTHER INFORMATION: Poly(proline) with 20 proline residues

<400> SEQUENCE: 13

Pro Pro Pro Pro Pro Pro Pro Pro Pro Pro Pro Pro Pro Pro Pro Pro
1               5                   10                  15

Pro Pro Pro Pro
            20

<210> SEQ ID NO 14
<211> LENGTH: 21
<212> TYPE: PRT
<213> ORGANISM: Artificial Sequence
<220> FEATURE:
<223> OTHER INFORMATION: Poly(proline) with 21 proline residues

<400> SEQUENCE: 14

Pro Pro Pro Pro Pro Pro Pro Pro Pro Pro Pro Pro Pro Pro Pro Pro
1               5                   10                  15

Pro Pro Pro Pro Pro
            20

<210> SEQ ID NO 15
<211> LENGTH: 9
<212> TYPE: PRT

<213> ORGANISM: Artificial Sequence
<220> FEATURE:
<223> OTHER INFORMATION: Poly(proline)
<220> FEATURE:
<221> NAME/KEY: misc_feature
<222> LOCATION: (9)..(9)
<223> OTHER INFORMATION: where X = 1-78 proline residues

<400> SEQUENCE: 15

Pro Pro Pro Pro Pro Pro Pro Pro Xaa
1               5

<210> SEQ ID NO 16
<211> LENGTH: 86
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (86)..(86)
<223> OTHER INFORMATION: where Xaa = 1-176 proline residues

<400> SEQUENCE: 16

Pro Pro Pro Pro Pro Pro Pro Pro Pro Pro Pro Pro Pro Pro Pro
1               5                   10                  15

Pro Pro Pro Pro Pro Pro Pro Pro Pro Pro Pro Pro Pro Pro Pro
                20                  25                  30

Pro Pro Pro Pro Pro Pro Pro Pro Pro Pro Pro Pro Pro Pro Pro
            35                  40                  45

Pro Pro Pro Pro Pro Pro Pro Pro Pro Pro Pro Pro Pro Pro Pro
        50                  55                  60

Pro Pro Pro Pro Pro Pro Pro Pro Pro Pro Pro Pro Pro Pro Pro
65                  70                  75                  80

Pro Pro Pro Pro Pro Xaa
                85

<210> SEQ ID NO 17
<211> LENGTH: 262
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (262)..(262)
<223> OTHER INFORMATION: where Xaa is one or more proline residues

<400> SEQUENCE: 17

Pro Pro Pro Pro Pro Pro Pro Pro Pro Pro Pro Pro Pro Pro Pro
1               5                   10                  15

Pro Pro Pro Pro Pro Pro Pro Pro Pro Pro Pro Pro Pro Pro Pro
                20                  25                  30

Pro Pro Pro Pro Pro Pro Pro Pro Pro Pro Pro Pro Pro Pro Pro
            35                  40                  45

Pro Pro Pro Pro Pro Pro Pro Pro Pro Pro Pro Pro Pro Pro Pro
        50                  55                  60

Pro Pro Pro Pro Pro Pro Pro Pro Pro Pro Pro Pro Pro Pro Pro
65                  70                  75                  80

Pro Pro Pro Pro Pro Pro Pro Pro Pro Pro Pro Pro Pro Pro Pro
                85                  90                  95

Pro Pro Pro Pro Pro Pro Pro Pro Pro Pro Pro Pro Pro Pro Pro
            100                 105                 110

```
Pro Pro Pro Pro Pro Pro Pro Pro Pro Pro Pro Pro Pro
        115                 120                 125

Pro Pro Pro Pro Pro Pro Pro Pro Pro Pro Pro Pro Pro
        130                 135                 140

Pro Pro Pro Pro Pro Pro Pro Pro Pro Pro Pro Pro Pro
145                 150                 155                 160

Pro Pro Pro Pro Pro Pro Pro Pro Pro Pro Pro Pro
        165                 170                 175

Pro Pro Pro Pro Pro Pro Pro Pro Pro Pro Pro Pro
        180                 185                 190

Pro Pro Pro Pro Pro Pro Pro Pro Pro Pro Pro Pro
        195                 200                 205

Pro Pro Pro Pro Pro Pro Pro Pro Pro Pro Pro Pro
        210                 215                 220

Pro Pro Pro Pro Pro Pro Pro Pro Pro Pro Pro Pro
225                 230                 235                 240

Pro Pro Pro Pro Pro Pro Pro Pro Pro Pro Pro Pro
        245                 250                 255

Pro Pro Pro Pro Pro Xaa
        260

<210> SEQ ID NO 18
<211> LENGTH: 10
<212> TYPE: PRT
<213> ORGANISM: Artificial Sequence
<220> FEATURE:
<223> OTHER INFORMATION: Poly(glutamic acid) with 10 Glu residues

<400> SEQUENCE: 18

Glu Glu Glu Glu Glu Glu Glu Glu Glu Glu
1               5                   10

<210> SEQ ID NO 19
<211> LENGTH: 2
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (2)..(2)
<223> OTHER INFORMATION: where Xaa = n Pro residue(s)

<400> SEQUENCE: 19

Pro Xaa
1

<210> SEQ ID NO 20
<211> LENGTH: 50
<212> TYPE: PRT
<213> ORGANISM: Artificial Sequence
<220> FEATURE:
<223> OTHER INFORMATION: Poly(lysine) with 50 Lys residues

<400> SEQUENCE: 20

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
        35                  40                  45
```

Lys Lys
    50

<210> SEQ ID NO 21
<211> LENGTH: 110
<212> TYPE: PRT
<213> ORGANISM: Artificial Sequence
<220> FEATURE:
<223> OTHER INFORMATION: Poly(glutamic acid) with 110 Glu residues

<400> SEQUENCE: 21

Glu Glu Glu Glu Glu Glu Glu Glu Glu Glu Glu Glu Glu Glu Glu Glu
1               5                   10                  15

Glu Glu Glu Glu Glu Glu Glu Glu Glu Glu Glu Glu Glu Glu Glu Glu
            20                  25                  30

Glu Glu Glu Glu Glu Glu Glu Glu Glu Glu Glu Glu Glu Glu Glu Glu
        35                  40                  45

Glu Glu Glu Glu Glu Glu Glu Glu Glu Glu Glu Glu Glu Glu Glu Glu
    50                  55                  60

Glu Glu Glu Glu Glu Glu Glu Glu Glu Glu Glu Glu Glu Glu Glu Glu
65                  70                  75                  80

Glu Glu Glu Glu Glu Glu Glu Glu Glu Glu Glu Glu Glu Glu Glu Glu
                85                  90                  95

Glu Glu Glu Glu Glu Glu Glu Glu Glu Glu Glu Glu Glu Glu
            100                 105                 110

<210> SEQ ID NO 22
<211> LENGTH: 14
<212> TYPE: PRT
<213> ORGANISM: Artificial Sequence
<220> FEATURE:
<223> OTHER INFORMATION: Poly(proline)
<220> FEATURE:
<221> NAME/KEY: misc_feature
<222> LOCATION: (14)..(14)
<223> OTHER INFORMATION: where Xaa = 1-11 Pro residues

<400> SEQUENCE: 22

Pro Pro Pro Pro Pro Pro Pro Pro Pro Pro Pro Pro Pro Xaa
1               5                   10

<210> SEQ ID NO 23
<211> LENGTH: 44
<212> TYPE: PRT
<213> ORGANISM: Artificial Sequence
<220> FEATURE:
<223> OTHER INFORMATION: Poly(hydroxyproline)
<220> FEATURE:
<221> NAME/KEY: misc_feature
<222> LOCATION: (1)..(44)
<223> OTHER INFORMATION: where Xaa = hydroxyproline

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa
        35                  40